(12) United States Patent
Hopkins et al.

(10) Patent No.: US 9,353,087 B2
(45) Date of Patent: May 31, 2016

(54) INHIBITORS OF BRUTON'S TYROSINE KINASE

(71) Applicants: Biogen Idec MA Inc., Cambridge, MA (US); Sunesis Pharmaceuticals, Inc., South San Francisco, CA (US)

(72) Inventors: Brian T. Hopkins, Newton, MA (US); Xiongwei Cai, Weston, MA (US); Timothy R. Chan, Newton, MA (US); Patrick Conlon, Wakefield, MA (US); Michael Humora, Weston, MA (US); Tracy J. Jenkins, Watertown, MA (US); Michael J. Macphee, Weston, MA (US); Xianglin Shi, Weston, MA (US); Ross A. Miller, South Plainfield, NJ (US); Andrew Thompson, South Plainfield, NJ (US)

(73) Assignees: Biogen MA Inc., Cambridge, MA (US); Sunesis Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/406,081

(22) PCT Filed: Jun. 7, 2013

(86) PCT No.: PCT/US2013/044797
§ 371 (c)(1),
(2) Date: Dec. 5, 2014

(87) PCT Pub. No.: WO2013/185082
PCT Pub. Date: Dec. 12, 2013

(65) Prior Publication Data
US 2015/0126528 A1 May 7, 2015

Related U.S. Application Data

(60) Provisional application No. 61/657,369, filed on Jun. 8, 2012.

(51) Int. Cl.
*A61K 31/506* (2006.01)
*C07D 401/14* (2006.01)

(52) U.S. Cl.
CPC ........... *C07D 401/14* (2013.01); *C07B 2200/13* (2013.01)

(58) Field of Classification Search
CPC ............................ C07D 401/14; A61K 31/506
See application file for complete search history.

(56) References Cited

U.S. PATENT DOCUMENTS

| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 7,528,143 | B2 * | 5/2009 | Noronha et al. ............... 514/275 |
| 8,293,923 | B2 * | 10/2012 | Guckian et al. ............. 548/305.1 |
| 8,785,440 | B2 * | 7/2014 | Bui et al. .................... 514/235.8 |
| 9,029,359 | B2 * | 5/2015 | Bui et al. .................... 514/211.15 |
| 2009/0298869 | A1 | 12/2009 | Burnier et al. |
| 2011/0152260 | A1 * | 6/2011 | Guckian et al. ............. 514/234.5 |
| 2012/0058996 | A1 | 3/2012 | Liu et al. |
| 2012/0157442 | A1 * | 6/2012 | Bui et al. ................. 514/211.15 |
| 2012/0157443 | A1 * | 6/2012 | Bui et al. ................. 514/211.15 |
| 2013/0345192 | A1 * | 12/2013 | Hopkins et al. .......... 514/210.18 |
| 2014/0309212 | A1 | 10/2014 | Bui et al. |
| 2015/0158843 | A1 * | 6/2015 | Hopkins et al. ............... 514/275 |

FOREIGN PATENT DOCUMENTS

| WO | WO-96/05309 A2 | 2/1996 | |
| WO | WO 2010077836 A2 * | 7/2010 | ........... C07D 417/12 |
| WO | WO-2011/029043 A1 | 3/2011 | |
| WO | WO 2011029046 A1 * | 3/2011 | |
| WO | WO-2012/022265 A1 | 2/2012 | |
| WO | WO-2012/058645 A1 | 5/2012 | |
| WO | WO-2013/185084 A1 | 12/2013 | |

OTHER PUBLICATIONS

National Cancer Institute (http://www.cancer.gov/) (Downloaded May 29, 2014).*
J. Luo et al., 36 Cell, 823-837 (2009).*
H.A. Fine, Neoplasms of the Central Nervous System in, 2 Cancer Principles & Practice of Oncology 1834-1887 (V.T. DeVita, Jr. et al. eds., 5th ed., 2005).*
D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
S.K. Bhatia et al., Autoimmunity and autoimmune disease in 6 Principles of Medical Biology 239-263, 244 (1996).*
S.M. Hayter et al., Autoimmunity Reviews, 754-765, 756 (2012).*
Kinase Inhibitors, Methods in Molecular Biology (B. Kuster ed., 2012).*
T.A. Denison et al., Heterogeneity of Cancers and Its Implication for Targeted Drug Delivery in, Cancer Targeted Drug Delivery an Elusive Dream, 337-362 (Y.H. Bae et al., eds., 2013).*
K-H Kim et al., 21 Bioorganic & Medicinal Chemistry Letters, 6258-6263 (2011).*
Z. Pan et al., 2 ChemMedChem, 58-61 (2007).*
A. Flemming et al., 9 Nature Reviews | Drug Discovery (2010).*
L.R. Whyburn et al., 171 Journal of Immunology, 1850-1858 (2003).*
A.O. Vassilev et al., 10 Current Pharmaceutical Design, 1757-1766 (2004).*

(Continued)

*Primary Examiner* — Alexander R Pagano
(74) *Attorney, Agent, or Firm* — Choate, Hall & Stewart, LLP; John P. Rearick

(57) ABSTRACT

The present invention provides a compound, solid forms, and compositions thereof, which are useful as inhibitors of Bruton's tyrosine kinase and which exhibit desirable characteristics for the same. The present invention also provides methods of making provided compound and solid forms.

19 Claims, 7 Drawing Sheets

(56) References Cited

OTHER PUBLICATIONS

Faith Uckun et al., 136 British Journal of Haematology, 574-589 (2007).*
R.W. Hendriks et al., 18 Seminars in Immunology, 67-76 (2006).*
Faith Uckun et al., 20 Expert Opinion on Therapeutic Patents, 1457-1470 (2010).*
U. McDermott et al., 27 Journal of Clinical Oncology, 5650-5659 (2009).*
C.L. Sawyers, Nature, 548-552 (2008).*
C.M. Coughlin et al., Breast Cancer Research Treatment, 1-11 (2010).*
Banda, N.K. et al., Complement activation pathways in murine immune complex-induced arthritis and in C3a and C5a generation in vitro, Clin. Exp. Immunol., 159(1):100-8(2010).
Brown, A.M. and Rampe, D., Drug-Induced Long QT Syndrome: Is HERG the Root of All Evil, Pharmaceutical News, 7(4):15-20 (2000).
Chan, O.T. et al., The central and multiple roles of B cells in lupus pathogenesis, Immunol. Rev., 169:107-21 (1999).
Cohen, S.B. et al., Reflex Trial Group. Rituximab for rheumatoid arthritis refractory to anti-tumor necrosis factor therapy: Results of a multicenter, randomized, double-blind, placebo-controlled, phase III trial evaluating primary efficacy and safety at twenty-four weeks, Arthritis Rheum., 54(9):2793-806 (2006).
Furie, R. et al., Bliss-76 Study Group. A phase III, randomized, placebo-controlled study of belimumab, a monoclonal antibody that inhibits B lymphocyte stimulator, in patients with systemic lupus erythematosus, Arthritis Rheum., 63(12):3918-30 (2011).
Goldschmidt, T.J. and Holmdahl, R., Therapeutic effects of monoclonal antibodies to alpha beta TCR but not to CD4 on collagen-induced arthritis in the rat, Cell Immunol, 154(1):240-8 (1994).
Helfgott, S.M. et al., Suppressive effects of anti-mu serum on the development of collagen arthritis in rats, Clin. Immunol. Immunopathol., 31(3):403-11 (1984).
Holmdahl, R. et al., Chronicity of arthritis induced with homologous type II collagen (CII) in rats is associated with anti-CII B-cell activation, J. Autoimmun., 7(6):739-52 (1994).
Honigberg, L.A. et al., The Bruton tyrosine kinase inhibitor PCI-32765 blocks B-cell activation and is efficacious in models of autoimmune disease and B-cell malignancy, Proc Natl Acad Sci U S A., 107(29):13075-80 (2010).
International Search Report for PCT/US2013/044797, 4 pages (Feb. 12, 2014).
Kagari, T. et al., Essential role of Fc gamma receptors in anti-type II collagen antibody-induced arthritis, J. Immunol., 170(8):4318-24 (2003).
Navarra, S.V. et al., Bliss-52 Study Group. Efficacy and safety of belimumab in patients with active systemic lupus erythematosus: a randomised, placebo-controlled, phase 3 trial, Lancet, 377(9767):721-31 (2011).
Panayi, G. S. et al., Pathogenesis of rheumatoid arthritis, The role of T cells and other beasts, Rheum. Dis. Clin. North Am., 27(2):317-34 (2001).
Stuart, J.M. et al., Type II collagen-induced arthritis in rats. Passive transfer with serum and evidence that IgG anticollagen antibodies can cause arthritis, J. Exp. Med., 155(1):1-16 (1982).
Weirich, J. and Antoni, H., Rate-dependence of antiarrhythmic and proarrhythmic properties of class I and class III antiarrhythmic drugs, Basic Res. Cardiol., 93 Suppl 1:125-32 (1998).
Written Opinion for PCT/US2013/044797, 10 pages (Feb. 12, 2014).
Yap, Y.G. and Camm, A.J., Arrhythmogenic mechanisms of non-sedating antihistamines, Clin. Exp. Allergy, 29 Suppl 3:174-81 (1999).
Zhang, Z. and Bridges, S.L. Jr., Pathogenesis of rheumatoid arthritis, Role of B lymphocytes, Rheum. Dis. Clin. North Am., 27(2):335-53 (2001).

* cited by examiner

Figure 1: X-ray Powder Diffraction
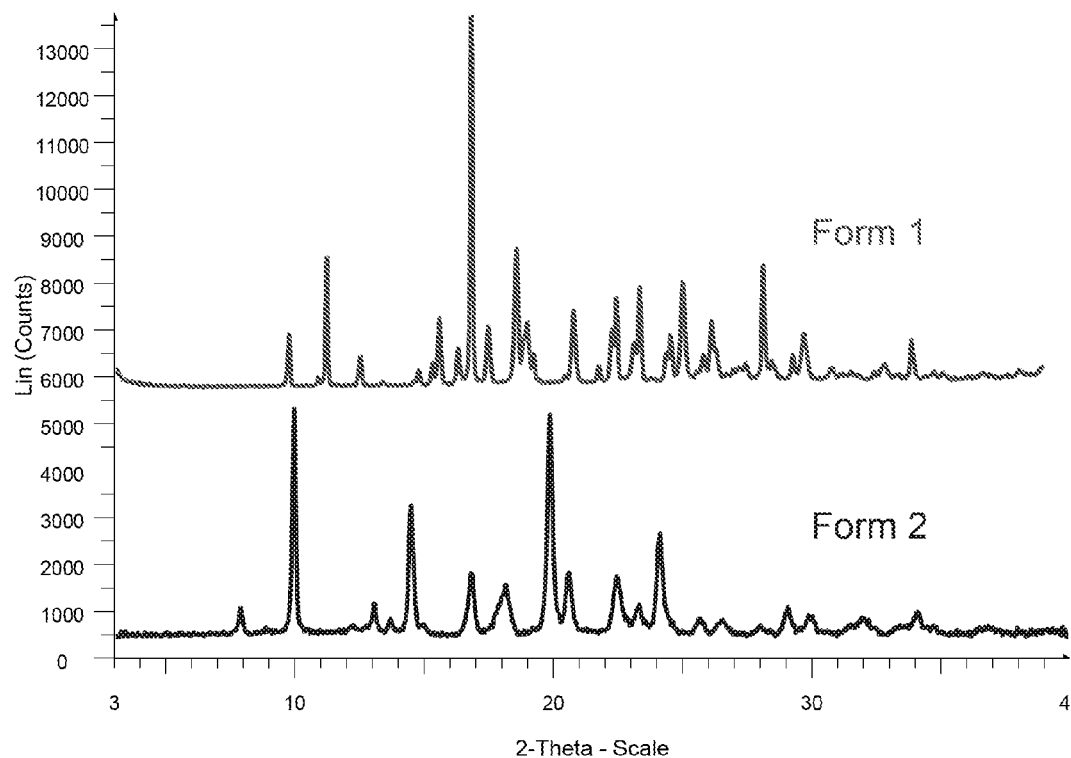

Figure 2: DVS / Hygroscopicity of Form 1
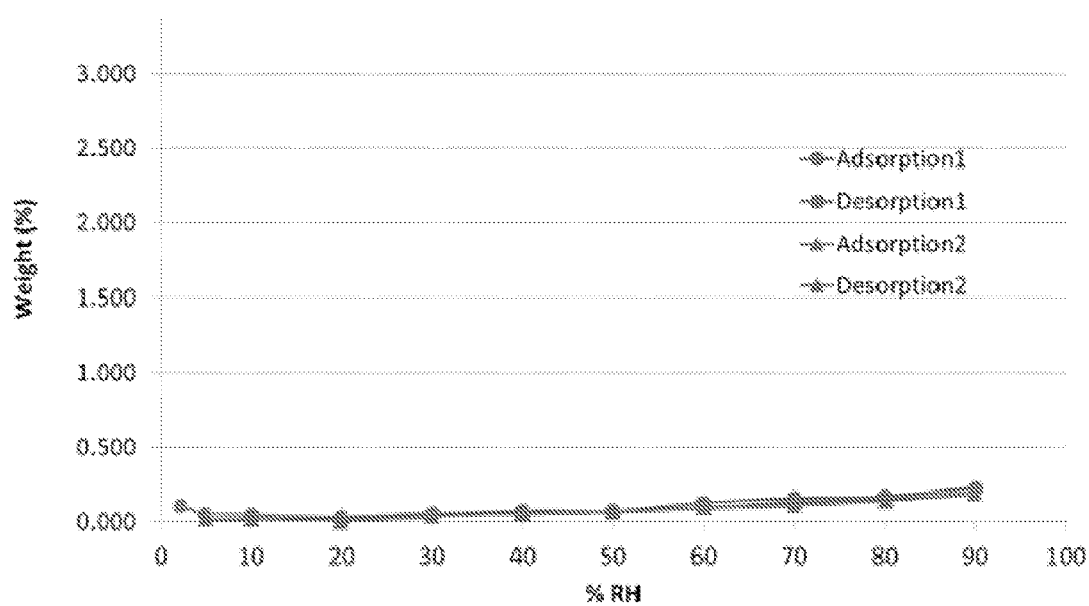

Figure 3: Differential Scanning Calorimetry
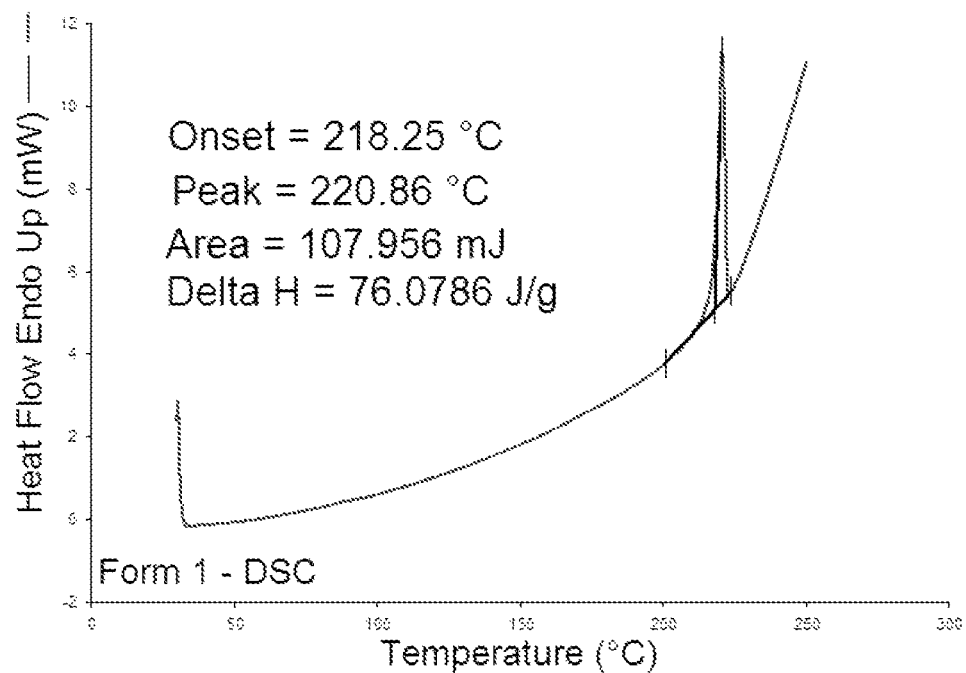
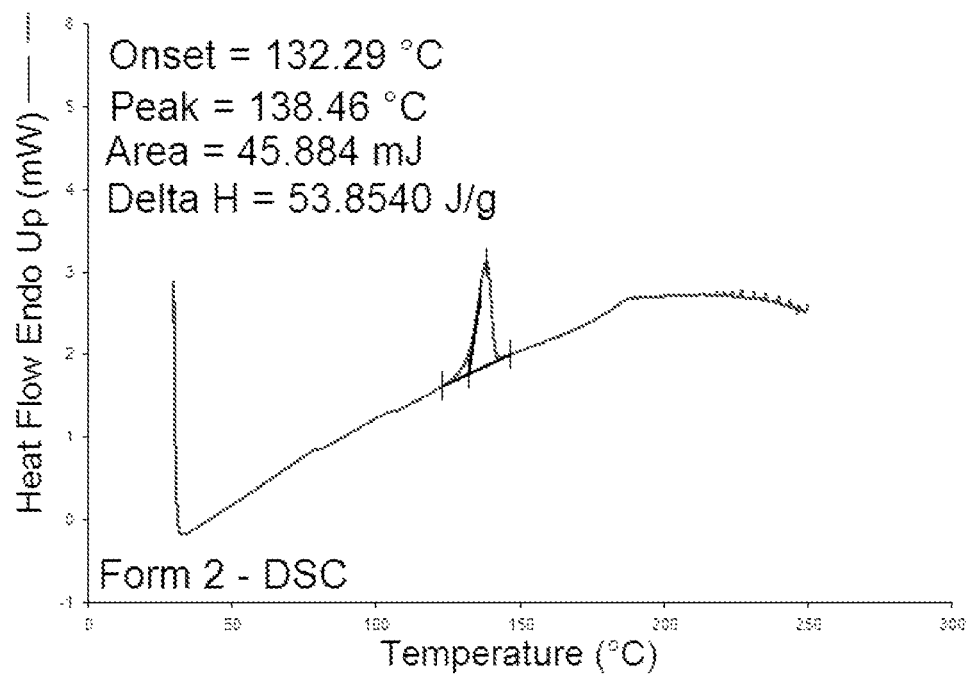

Figure 4: Rat Collagen-Induced Arthritis
A
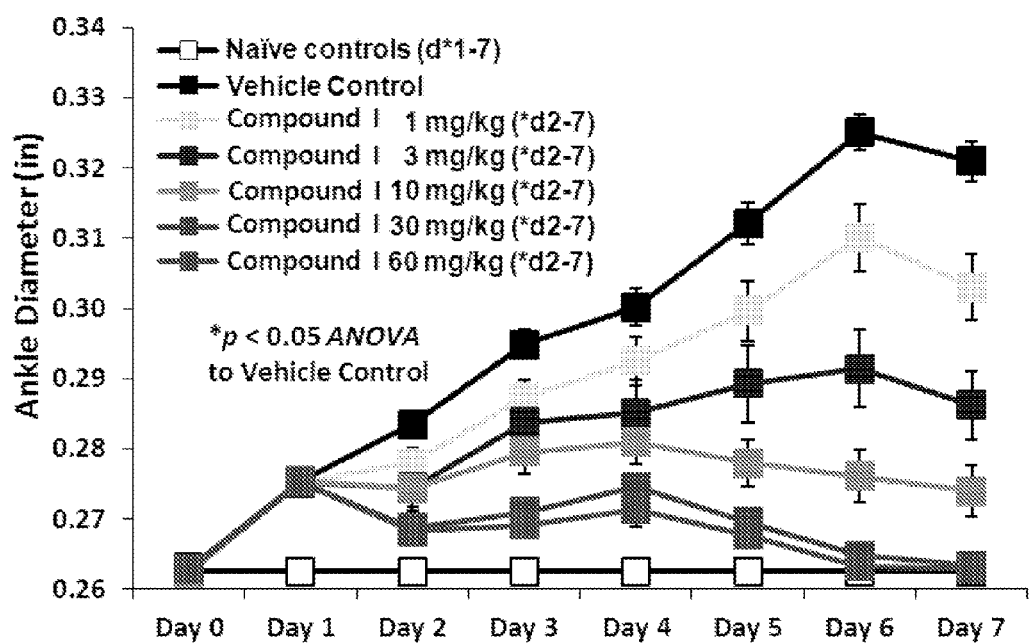
B
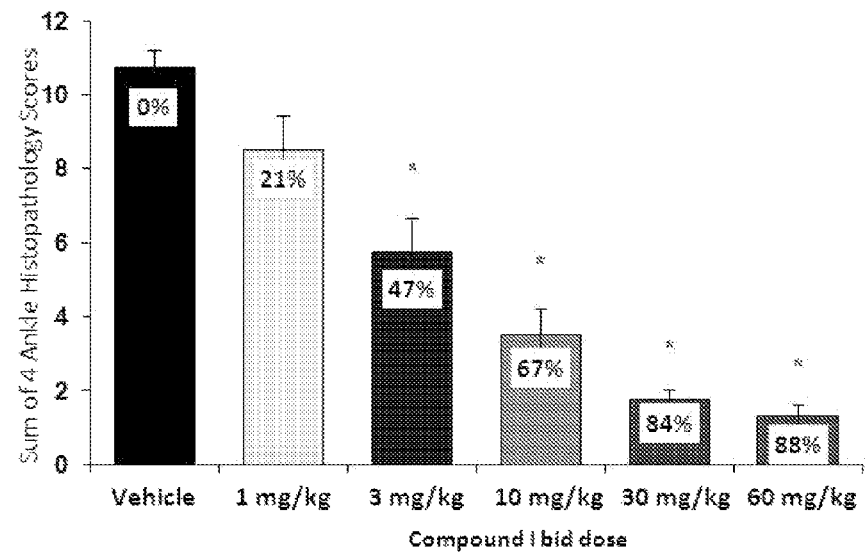

Figure 5: Phosphorylation of PLCγ2
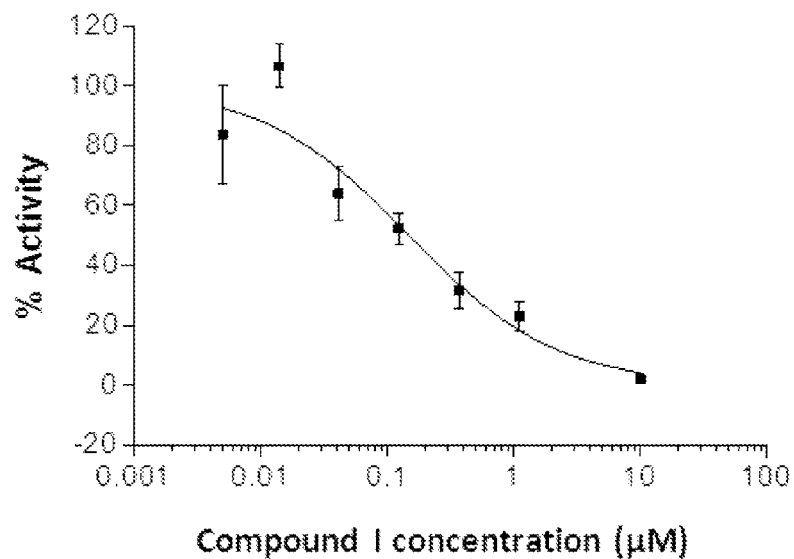
Figure 6: Anti-IgM-Mediated Human B Cell Proliferation
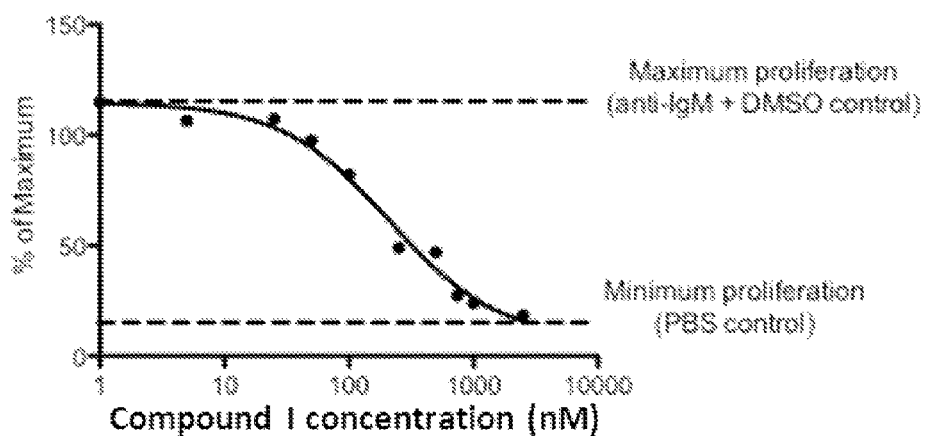

Figure 7: Fc-Receptor Dependent Cytokine Expression by Activated Macrophages
A
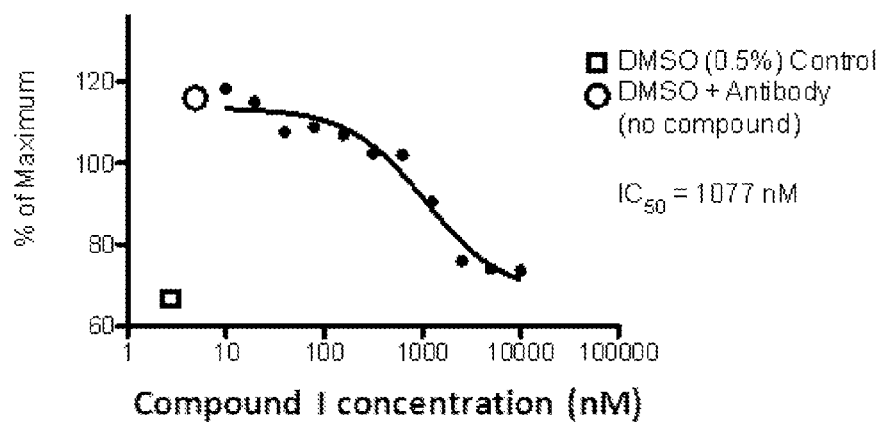
B
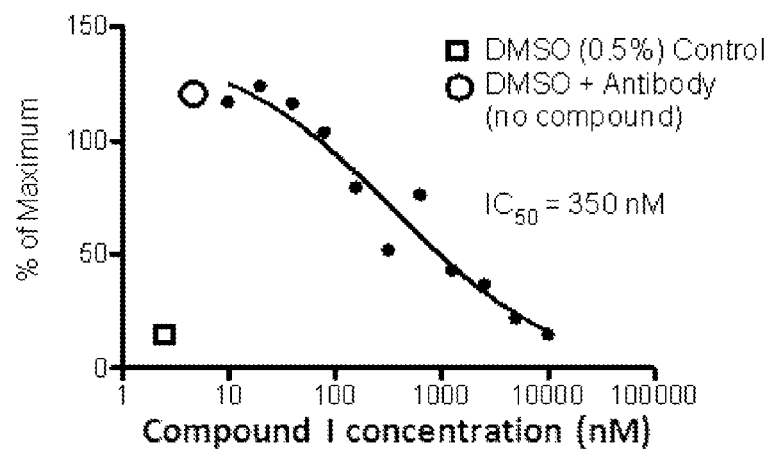

INHIBITORS OF BRUTON'S TYROSINE KINASE

CROSS REFERENCE TO RELATED APPLICATIONS

The present application claims priority to U.S. provisional application Ser. No. 61/657,369, filed Jun. 8, 2012, the entire contents of which are hereby incorporated herein by reference.

BACKGROUND OF THE INVENTION

The Tec kinases are non-receptor tyrosine kinases including: Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk), Lck (lymphocyte-specific protein tyrosine kinase), and Bmx (bone-marrow tyrosine kinase gene on chromosome X; also known as Etk)). These kinases are primarily expressed in haematopoietic cells, although expression of Bmx and Tec has been detected in endothelial and liver cells. Tec kinases (Itk, Rlk and Tec) are expressed in T cells and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors for Tec kinases such as Btk. The present invention fulfills these and other needs.

SUMMARY OF THE INVENTION

The present invention provides, among other things, a novel compound, solid forms thereof, and compositions thereof, which are useful as inhibitors of one or more Tec kinases and exhibit desirable characteristics for the same. In general, the compound, solid forms, and pharmaceutically acceptable compositions thereof, are useful for treating or lessening the severity of a variety of diseases or disorders as described in detail herein. The present invention further provides methods of making the compounds and solid forms disclosed herein.

BRIEF DESCRIPTION OF THE DRAWINGS

FIG. 1 depicts the x-ray powder diffraction (XRPD) pattern for Forms 1 and 2 of Compound I.

FIG. 2 depicts the adsorption/desorption isotherm of Form 1 of Compound I.

FIG. 3 depicts Differential Scanning calorimetry (DSC) for forms of Compound I.

FIG. 4 depicts the dose dependent efficacy of Compound I in a rat model.

FIG. 5 depicts inhibition by Compound I of phosphorylation of PLCγ2 using electrochemiluminescence immunoassay in Ramos cells.

FIG. 6 depicts inhibition by Compound I of anti-IgM-mediated human B cell proliferation.

FIG. 7 depicts inhibition by Compound I of Fc-Receptor dependent cytokine expression by activated macrophages. FIG. 7A shows inhibition of TNFα, while FIG. 7B shows inhibition of IL-6.

DETAILED DESCRIPTION OF THE INVENTION

Figure 8:
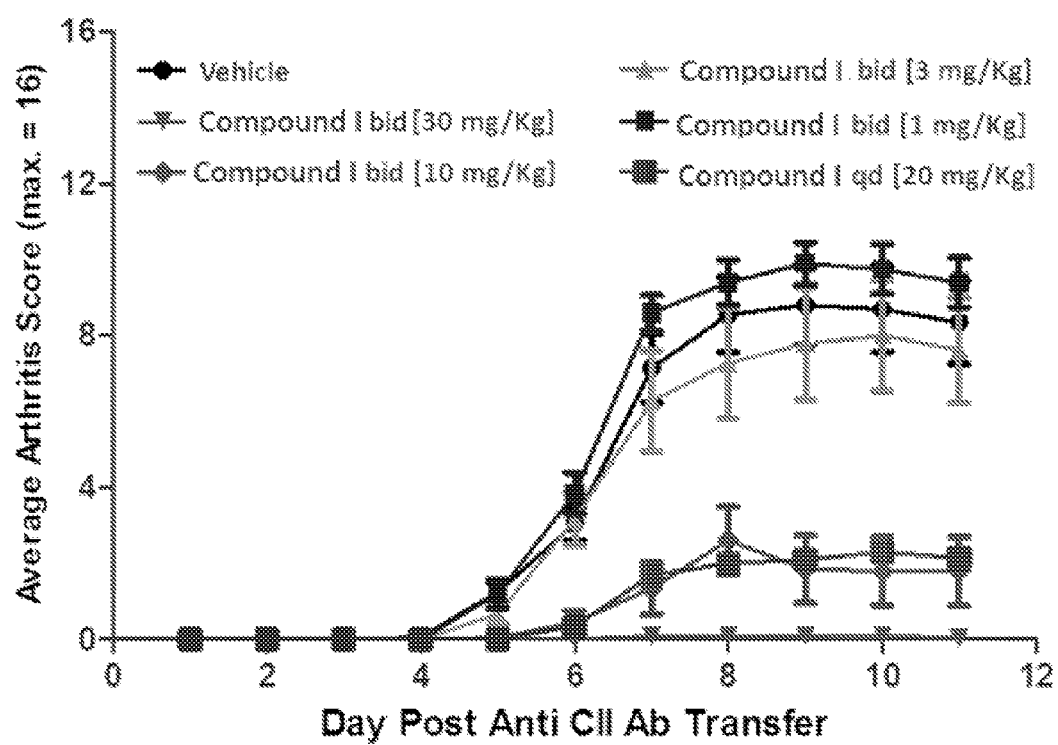
FIG. 8 depicts the dose dependent efficacy of Compound I in mouse collagen-antibody induced arthritis.

General Description of Certain Aspects of the Invention:

In certain embodiments, the present invention provides compound I:

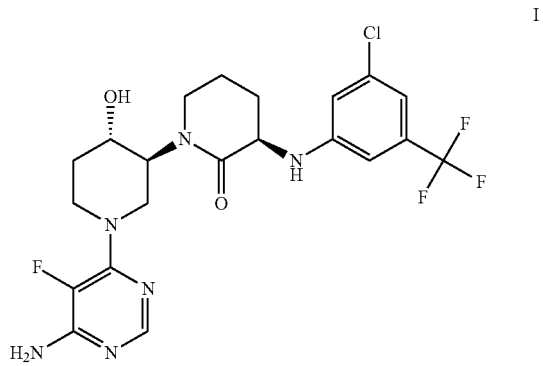 [SMILES: Nc1ncnc(N2CC[C@H](O)[C@@H](N3CCC[C@@H](Nc4cc(Cl)cc(C(F)(F)F)c4)C3=O)C2)c1F]

or a pharmaceutically acceptable salt thereof.

Compound I is active in a variety of assays and therapeutic models demonstrating inhibition of Bruton's tyrosine kinase (Btk). Notably, Compound I was found to inhibit Btk in both in vitro and in vivo models. Accordingly, Compound I is useful for treating one or more disorders associated with activity of Btk.

Compound I has unexpectedly been found to exhibit advantageous properties over known inhibitors of Btk. Without wishing to be bound by any particular theory, it is believed that Compound I possesses an improved off-target profile as measured by hERG inhibition, GSH reactive metabolite trapping, PXR induction assays, or a combination thereof. Experimental data showing such advantageous properties is provided in the ensuing Examples.

It would be desirable to provide a solid form of Compound I that has good aqueous solubility, stability, ease of formulation, and other desirable characteristics. Accordingly, the present invention provides several solid forms of Compound I.

According to one embodiment, the present invention provides an amorphous form, a crystalline form, or a mixture thereof. Exemplary solid forms are described in more detail below.

In some embodiments, the present invention provides Compound I substantially free of impurities. As used herein, the term "substantially free of impurities" means that the compound contains no significant amount of extraneous matter. Such extraneous matter may include starting materials, residual solvents, or any other impurities that may result from the preparation of, and/or isolation of, Compound I. In certain embodiments, at least about 95% by weight of Compound I is present. In still other embodiments of the invention, at least about 99% by weight of Compound I is present.

According to one embodiment, Compound I is present in an amount of at least about 95, 97, 97.5, 98.0, 98.5, 99, 99.5, 99.8 weight percent where the percentages are based on the total weight of the composition. According to another embodiment, Compound I contains no more than about 3.0 area percent HPLC of total organic impurities and, in certain embodiments, no more than about 1.5 area percent HPLC total organic impurities relative to the total area of the HPLC chromatogram. In other embodiments, Compound I contains no more than about 1.0 area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The present invention includes all tautomeric forms of Compound I. Additionally, the present invention also includes compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that Compound I can exist in a variety of solid forms. Such forms include polymorphs and amorphous forms. The solid forms can be solvates, hydrates and unsolvated forms of Compound I. All such forms are contemplated by the present invention. In certain embodiments, the present invention provides Compound I as a mixture of one or more solid forms of Compound I.

As used herein, the term "polymorph" refers to the different crystal structures (of solvated or unsolvated forms) in which a compound can crystallize.

As used herein, the term "solvate" refers to a solid form with either a stoichiometric or non-stoichiometric amount of solvent (e.g., a channel solvate). For polymorphs, the solvent is incorporated into the crystal structure. Similarly, the term "hydrate" refers to a solid form with either a stoichiometric or non-stoichiometric amount of water. For polymorphs, the water is incorporated into the crystal structure.

As used herein, the term "about", when used in reference to a degree 2-theta value refers to the stated value±0.3 degree 2-theta. In certain embodiments, "about" refers to ±0.2 degree 2-theta or ±0.1 degree 2-theta.

In certain embodiments, Compound I is a crystalline solid. In other embodiments, Compound 1 is a crystalline solid substantially free of amorphous Compound I. As used herein, the term "substantially free of amorphous Compound I" means that the compound contains no significant amount of amorphous Compound I (e.g., equal or greater than about 95% of crystalline Compound 1). In certain embodiments, at least about 95% by weight of crystalline Compound I is present. In still other embodiments of the invention, at least about 97%, 98% or 99% by weight of crystalline compound I is present.

In certain embodiments, Compound I is a neat or unsolvated crystal form and thus does not have any water or solvent incorporated into the crystal structure. It has been found that Compound I can exist in at least two distinct neat (i.e., anhydrous) crystal forms, or polymorphs. In some embodiments, the present invention provides a polymorphic form of Compound I referred to herein as Form 1. In other embodiments, the present invention provides a polymorphic form of Compound I referred to herein as Form 2.

In certain embodiments, the present invention provides Form 1 of Compound I. According to one embodiment, Form 1 of Compound I is characterized in that it has one or more peaks in its powder X-ray diffraction pattern selected from those at about 9.708, about 11.174, about 12.485, about 15.558, about 16.293, about 16.790, about 17.470, about 18.550, about 18.966, about 20.776, about 22.439, about 23.347, about 24.551, about 25.028, about 26.167, about 28.152, about 29.739, and about 33.922 degrees 2-theta. In some embodiments, Form 1 of Compound I is characterized in that it has two or more peaks in its powder X-ray diffraction pattern selected from those at about 9.708, about 11.174, about 12.485, about 15.558, about 16.293, about 16.790, about 17.470, about 18.550, about 18.966, about 20.776, about 22.439, about 23.347, about 24.551, about 25.028, about 26.167, about 28.152, about 29.739, and about 33.922 degrees 2-theta. In certain embodiments, Form 1 of Compound I is characterized in that it has three or more peaks in its powder X-ray diffraction pattern selected from those at about 9.708, about 11.174, about 12.485, about 15.558, about 16.293, about 16.790, about 17.470, about 18.550, about 18.966, about 20.776, about 22.439, about 23.347, about 24.551, about 25.028, about 26.167, about 28.152, about 29.739, and about 33.922 degrees 2-theta. In particular embodiments, Form 1 of Compound I is characterized in having substantially all of the peaks in its X-ray powder diffraction pattern selected from those at about 9.708, about 11.174, about 12.485, about 15.558, about 16.293, about 16.790, about 17.470, about 18.550, about 18.966, about 20.776, about 22.439, about 23.347, about 24.551, about 25.028, about 26.167, about 28.152, about 29.739, and about 33.922 degrees 2-theta. In an exemplary embodiment, Form 1 of Compound I is characterized in having substantially all of the peaks in its X-ray powder diffraction pattern selected from those at about:

| Compound I-Form 1 | |
|---|---|
| Peak | Angle 2-Theta ° |
| 1 | 9.708 |
| 2 | 11.174 |
| 3 | 12.485 |
| 4 | 15.558 |
| 5 | 16.293 |
| 6 | 16.790 |
| 7 | 17.470 |
| 8 | 18.550 |
| 9 | 18.966 |
| 10 | 20.776 |
| 11 | 22.439 |
| 12 | 23.347 |
| 13 | 24.551 |
| 14 | 25.028 |
| 15 | 26.167 |
| 16 | 28.152 |
| 17 | 29.739 |
| 18 | 33.922 |

According to one aspect, Form 1 of Compound I has a powder X-ray diffraction pattern substantially similar to that depicted in FIG. 1. According to another aspect, Form 1 of Compound I has a melting point of 220.9° C. Dynamic vapor sorption of Form 1 is shown in FIG. 2. It was observed that during the drying phase all water is lost without hysteresis, and that Form 1 is non-hygroscopic.

According to yet another aspect, Form 1 of Compound I has a differential scanning calorimetry pattern substantially similar to that depicted in FIG. 3. Form 1 of Compound I can be characterized by substantial similarity to two or more of these figures simultaneously.

Form 1 of Compound I may also be characterized by particle size distribution, as shown in Table 1 below for 3 different lots of Form 1.

TABLE 1

| Particle size distribution for Form 1. | | | |
|---|---|---|---|
| Form 1 | Particle Size (μm) | | |
| lot # | D10 | D50 | D90 |
| Lot 1 | 4.82 | 20.40 | 41.70 |
| Lot 2 | 2.66 | 19.96 | 47.63 |
| Lot 3 | 4.57 | 14.36 | 35.01 |

In certain embodiments, the present invention provides Form 2 of Compound I. According to one embodiment, Form 2 of Compound I is characterized in that it has one or more peaks in its powder X-ray diffraction pattern selected from those at about 7.834, about 8.826, about 9.886, about 13.030, about 14.429, about 16.779, about 18.108, about 19.835, about 20.561, about 22.426, and about 24.089 degrees 2-theta. In some embodiments, Form 2 of Compound I is characterized in that it has two or more peaks in its powder X-ray diffraction pattern selected from those at about 7.834, about 8.826, about 9.886, about 13.030, about 14.429, about 16.779, about 18.108, about 19.835, about 20.561, about 22.426, and about 24.089 degrees 2-theta. In certain embodiments, Form 2 of Compound I is characterized in that it has three or more peaks in its powder X-ray diffraction pattern selected from those at about 7.834, about 8.826, about 9.886, about 13.030, about 14.429, about 16.779, about 18.108, about 19.835, about 20.561, about 22.426, and about 24.089 degrees 2-theta. In particular embodiments, Form 2 of Compound I is characterized in having substantially all of the peaks in its X-ray powder diffraction pattern selected from those at about 7.834, about 8.826, about 9.886, about 13.030, about 14.429, about 16.779, about 18.108, about 19.835, about 20.561, about 22.426, and about 24.089 degrees 2-theta. In an exemplary embodiment, Form 2 of Compound 1 is characterized in having substantially all of the peaks in its X-ray powder diffraction pattern selected from those at about:

| Compound I - form 2 | |
|---|---|
| Peak | Angle 2-Theta ° |
| 1 | 7.834 |
| 2 | 8.826 |
| 3 | 9.886 |
| 4 | 13.030 |
| 5 | 14.429 |
| 6 | 16.779 |
| 7 | 18.108 |
| 8 | 19.835 |
| 9 | 20.561 |
| 10 | 22.426 |
| 11 | 24.089 |

According to one aspect, Form 2 of Compound I has a powder X-ray diffraction pattern substantially similar to that depicted in FIG. 1. According to another aspect, Form 2 of Compound I has a melting point of 138.5° C.

According to yet another aspect, Form 2 of Compound I has a differential scanning calorimetry pattern substantially similar to that depicted in FIG. 3. Form 2 of Compound I can be characterized by substantial similarity to both of these figures simultaneously.

According to another embodiment, the present invention provides Compound I as an amorphous solid. Amorphous solids are well known to one of ordinary skill in the art and are typically prepared by such methods as lyophilization, melting, spray drying, and precipitation from supercritical fluid, among others.

Synthesis of Compounds

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.)

In one aspect, the present invention provides methods for the synthesis of compound I, solid forms thereof, and intermediates thereto. In some embodiments, such methods are as shown in Scheme A, below:

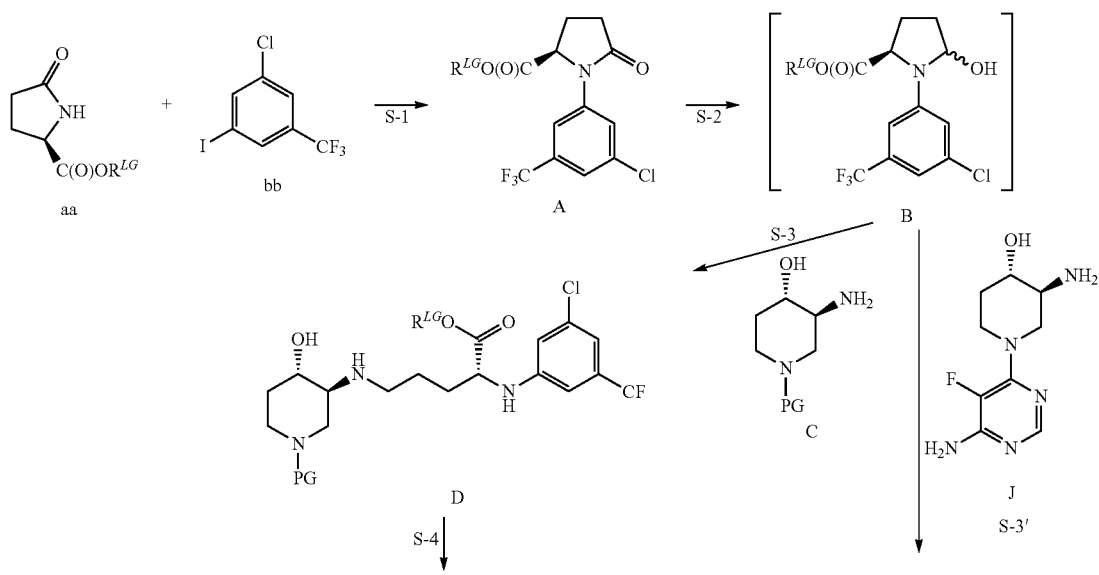

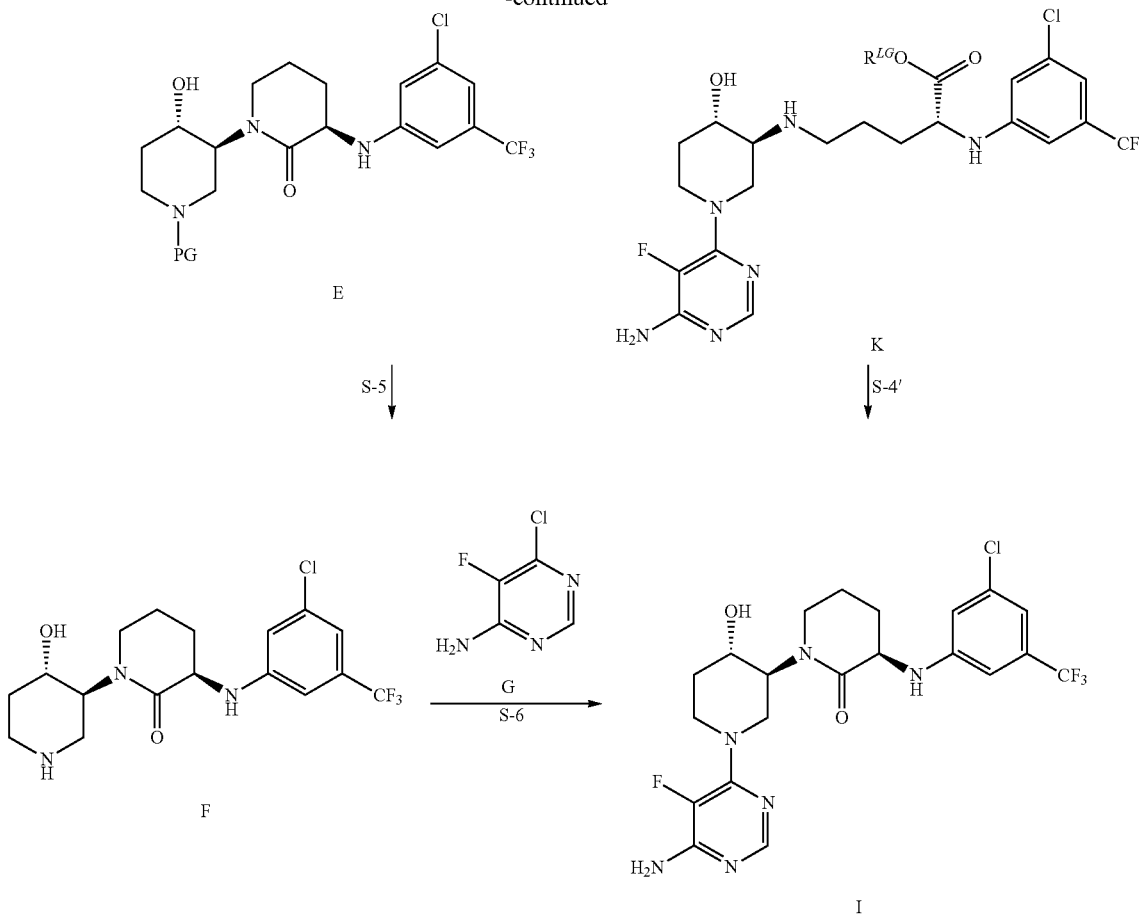

wherein each of —OR$^{LG}$ and PG are described below.

At step S-1, pyrrolidinone of formula aa is reacted under suitable conditions with aryl iodide bb to provide a pyrrolidinone of formula A. The —OR$^{LG}$ group of formula aa is a suitable leaving group. One of ordinary skill in the art will appreciate that a variety of suitable leaving groups —OR$^{LG}$ can be used to facilitate the reaction described in step S-1, and all such suitable leaving groups are contemplated by the present invention. A suitable leaving group is a chemical group that is readily displaced by a desired incoming chemical moiety. In some embodiments, —OR$^{LG}$ is an alkoxy group. In some embodiments, —OR$^{LG}$ is a C$_{1-6}$ aliphatic alkoxy group. In some embodiments, —OR$^{LG}$ is ethoxy or t-butoxy.

Step S-1 may optionally employ a suitable base. Such suitable bases include inorganic and amine bases. In some embodiments, a base is selected from N,N'-dimethylethylenediamine (DMEDA), cesium carbonate, cesium fluoride, or combinations thereof. The coupling step S-1 may further employ a suitable copper salt. In some embodiments, a copper salt is copper iodide.

Step S-1 may employ a suitable solvent. Solvents suitable for use in step S-1 include polar aprotic solvents (i.e., THF, methyl-THF, dioxane, acetonitrile, and combinations thereof). In some embodiments, the solvent is dioxane. In some embodiments, the solvent is THF.

In some embodiments, step S-1 is carried about at temperatures of about 20-60° C. In certain embodiments, the temperature is about 40° C.

It will be appreciated that while a single enantiomer of formula aa is depicted, the other enantiomer may be employed in the reaction schemes described herein, to provide compounds having the opposite stereochemistry at that position.

In some embodiments, the present invention provides a method comprising the steps of: a) providing a pyrrolidinone of formula aa:

wherein —OR$^{LG}$ is a suitable leaving group; and
b) reacting the pyrrolidinone of formula aa under suitable conditions with aryl iodide bb:

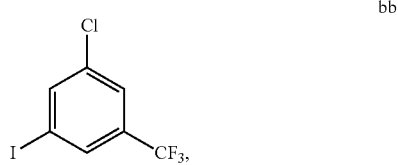 [SMILES: FC(F)(F)c1cc(Cl)cc(I)c1]

to provide a pyrrolidinone of formula A:

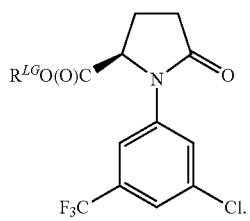

A

At step S-2, a pyrrolidinone of formula A is treated under suitable reducing conditions to provide a hemiaminal of formula B. In certain embodiments, the reducing conditions comprise a reducing agent. In some embodiments, a reducing agent is a metal hydride. In some embodiments, a reducing agent is an aluminium hydride. In some embodiments, a reducing agent is diisobutylaluminum hydride (DIBAL-H).

Step S-2 may employ a suitable solvent. Solvents suitable for use in step S-2 include polar aprotic solvents (i.e., THF, methyl-THF, dioxane, acetonitrile, and combinations thereof). In some embodiments, the solvent is methyl-THF. In some embodiments, the solvent is THF.

In some embodiments, step S-2 is carried about at temperatures of about −60-0° C. In certain embodiments, the temperature is about −35-20° C. In certain embodiments, the temperature is about −30° C.

In some embodiments, the present invention provides a method comprising the steps of:
a) providing a pyrrolidinone of formula A:

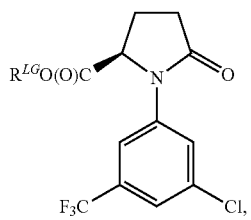

A wherein —OR$^{LG}$ is a suitable leaving group; and
b) reacting the pyrrolidinone of formula A with a suitable reducing agent to provide a hemiaminal of formula B:

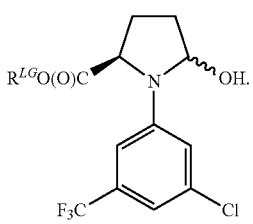

B

The synthesis may proceed from the hemiaminal of formula B in two directions, depending on the choice of amino alcohol used. At step S-3, protected amino alcohol of formula C is reacted under suitable conditions with a hemiaminal of formula B to provide an ester of formula D. The PG group of formula C is a suitable protecting group. Such amine protecting groups are known in the art and are described in detail in *Protecting Groups in Organic Synthesis*, T. W. Greene and P. G. M. Wuts, 3$^{rd}$ edition, John Wiley & Sons, 1999, the entirety of which is incorporated herein by reference. In some embodiments, a protecting group is a Boc group.

In some embodiments, step S-3 employs a reducing agent. Suitable reducing agents include metal hydrides, for example, borohydrides. In some embodiments, a reducing agent is sodium triacetoxy borohydride.

Step S-3 may employ a suitable solvent. Solvents suitable for use in step S-3 include polar aprotic solvents (i.e., THF, methyl-THF, dioxane, acetonitrile, DMSO, and combinations thereof). In some embodiments, the solvent is methyl-THF. In some embodiments, the solvent is DMSO.

In some embodiments, step S-3 is carried about at temperatures of about 20-80° C. In certain embodiments, the temperature is about 55° C.

In some embodiments, the present invention provides a method comprising the steps of:
a) providing an amino alcohol of formula C:

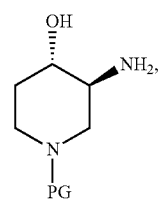

C and
b) reacting the amino alcohol of formula C with the hemiaminal of formula B under suitable conditions to provide an ester of formula D:

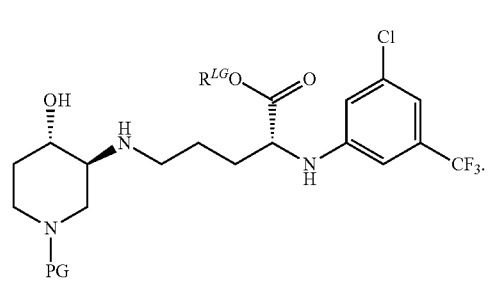

D

At step S-4, an ester of formula D is reacted under suitable conditions to provide a lactam of formula E. In some embodiments, step S-4 employs a suitable base. Such suitable bases are known in the art and can vary upon the choice of R$^{LG}$. In some embodiments, the base is an alkoxide. In some embodiments, the base is a silyloxy base. In certain embodiments, the base is potassium trimethylsilanolate (KOTMS).

Step S-4 may employ a suitable solvent. Solvents suitable for use in step S-4 include polar aprotic solvents (i.e., THF, methyl-THF, dioxane, acetonitrile, DMSO, and combinations thereof), or polar solvents such as alkyl alcohols, for example C$_1$ to C$_4$ alcohols (e.g. ethanol, methanol, 2-propanol). In some embodiments, the solvent is methyl-THF. In some embodiments, the solvent is ethanol.

Step S-4 may be carried out at a variety of temperatures. In some embodiments, the choice of temperature depends on whether a suitable base is employed. In some embodiments, reaction temperature is lower when using a base. In some embodiments, step S-4 uses a base and is carried about at temperatures of about −40-20° C. In certain embodiments, the temperature is about −20° C. In other embodiments, step S-4 is carried out at temperatures of about 20-100° C. In some embodiments, the temperature is about 75° C.

Step S-4 may optionally comprise a workup or crystallization step. In some embodiments, the lactam of formula E is recrystallized. In some embodiments, step S-4 comprises the addition of one or more solvents or anti-solvents to the lactam of formula E to effect crystallization. In some embodiments, the lactam of formula E is subjected to an aqueous workup, extracted with an organic solvent, and crystallized. In some embodiments, the organic solvent is ethyl acetate and an anti-solvent is added to effect crystallization. In some embodiments, the anti-solvent is hexanes.

In certain embodiments, the present invention provides a method comprising the step of reacting the ester of formula D with a suitable base to provide a lactam of formula E.

At step S-5, a lactam of formula E is deprotected to provide compound F. Suitable deprotection conditions will depend in part on the choice of protecting group. Such deprotection chemistries are known in the art and are described in detail Greene, supra. In some embodiments, when the protecting group is a Boc group, deprotection conditions employ a suitable acid. In certain embodiments, a suitable acid is an inorganic acid, a sulfonic acid, a carboxylic acid, or a Lewis acid. In some embodiments, the acid is HCl. In some embodiments, the acid is toluenesulfonic acid.

Step S-5 may employ a suitable solvent. Solvents suitable for use in step S-5 include polar solvents such as alkyl alcohols, for example $C_1$ to $C_4$ alcohols (e.g. ethanol, methanol, 2-propanol, 1-propanol), ethyl acetate, isopropyl acetate, THF, dioxane, or combinations thereof. In some embodiments, the solvent is isopropyl acetate. In some embodiments, the solvent is ethanol. In some embodiments, the solvent is butanol. In some embodiments, the solvent is 1-propanol.

In some embodiments, step S-5 is carried about at temperatures of about 0-60° C. In certain embodiments, the temperature is about 23° C.

In some embodiments, the present invention provides a method comprising the step of deprotecting the lactam of formula E to provide compound F.

At step S-6, pyrimidine G is reacted with compound F under suitable conditions to provide compound I. In some embodiments, step S-6 employs a suitable base. In some embodiments, a suitable base is an inorganic base, an amine base, or a combination thereof. In some embodiments, the base is a carbonate. In some embodiments, a base is sodium bicarbonate. In some embodiments, a base is diisopropylethyl amine. In some embodiments, a base is triethylamine.

In some embodiments, step S-6 is carried about at temperatures of about 60-120° C. In certain embodiments, the temperature is about 100° C. In certain embodiments, the temperature is about 115° C.

Step S-6 may employ a suitable solvent. Solvents suitable for use in step S-6 include polar solvents such as alkyl alcohols, for example $C_1$ to $C_4$ alcohols (e.g. ethanol, methanol, 2-propanol, 1-propanol), ethyl acetate, isopropyl acetate, THF, methyl-THF, dioxane, or combinations thereof. In some embodiments, the solvent is 1-propanol or t-butanol.

In some embodiments, the present invention provides a method comprising the steps of:
a) providing pyrimidine G:

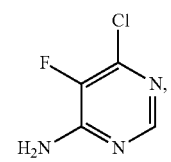

and
b) contacting the pyrimidine G with the compound of formula F under suitable conditions to provide compound I:

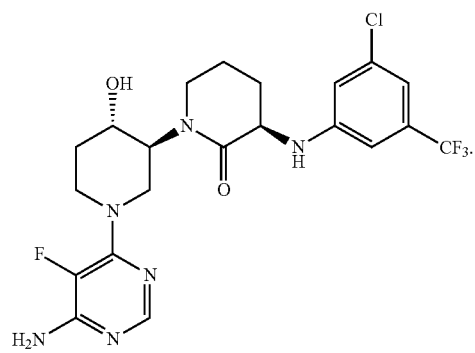

At step S-3″, amino alcohol of formula J is reacted under suitable conditions with a hemiaminal of formula B to provide an ester of formula K.

In some embodiments, step S-3′ employs a reducing agent. Suitable reducing agents include metal hydrides, for example, borohydrides. In some embodiments, a reducing agent is sodium triacetoxy borohydride.

Step S-3″ may employ a suitable solvent. Solvents suitable for use in step S-3″ include polar aprotic solvents (i.e., THF, methyl-THF, dioxane, acetonitrile, DMSO, and combinations thereof). In some embodiments, the solvent is methyl-THF. In some embodiments, the solvent is DMSO.

In some embodiments, step S-3′ is carried about at temperatures of about 20-80° C. In certain embodiments, the temperature is about 20° C.

In some embodiments, the present invention provides a method comprising the steps of:
a) providing amino alcohol J:

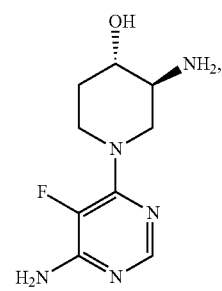

and b) reacting amino alcohol J with the hemiaminal of formula B under suitable conditions to provide an ester of formula K:

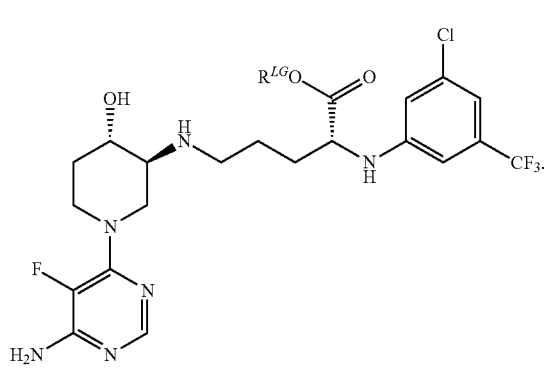

At step S-4', the ester of formula K is reacted under suitable conditions to provide Compound I. In some embodiments, step S-4' employs a suitable acid and optionally additional amide coupling reactions. Such suitable acid and reagents are known in the art and can vary upon the choice of $R^{LG}$. In certain embodiments, a suitable acid is an inorganic acid, a sulfonic acid, a carboxylic acid, or a Lewis acid. In some embodiments, the acid is HCl.

Step S-4' may employ additional coupling reagents. In certain embodiments, a peptide coupling reagent is selected from a carbodiimide or triazole activating reagent. In some embodiments, a peptide coupling reagents is selected from FDPP, PFPOH, BOP-Cl, EDC, EDCA, DCC, DIC, HOBt, HOAt, HBTU, HATU, HCTU, TBTU, and PyBOP. In some embodiments, a peptide coupling reagent is selected from EDCA, HOBt, or a combination thereof.

Step S-4' may employ a suitable solvent. Solvents suitable for use in step S-4' include polar aprotic solvents (i.e., THF, methyl-THF, dioxane, acetonitrile, DMSO, and combinations thereof), or polar solvents such as alkyl alcohols, for example $C_1$ to $C_4$ alcohols (e.g. ethanol, methanol, 2-propanol). In some embodiments, the solvent is methyl-THF. In some embodiments, the solvent is ethanol.

In certain embodiments, the present invention provides a method comprising the step of reacting the ester of formula K with a suitable base to provide Compound I.

In some embodiments, any of steps S-1, S-2, S-3, S-3', S-4, S-4', S-5, and S-6 may comprise a recrystallization step. In some embodiments, such a recrystallization step comprises the addition of one or more solvents or anti-solvents to effect crystallization. In some embodiments, a step comprises recrystallization from a mixture of ethanol and water.

In certain embodiments, each of the aforementioned synthetic steps may be performed sequentially with isolation of each intermediate performed after each step. Alternatively, each of steps S-1, S-2, S-3, S-3', S-4, S-4', S-5, and S-6, as depicted in Scheme A above, may be performed in a manner whereby no isolation of one or more intermediates A, B, D, E, F, H, or K is performed.

In certain embodiments, all the steps of the aforementioned synthesis may be performed to prepare the desired final product. In other embodiments, two, three, four, five, or more sequential steps may be performed to prepare an intermediate or the desired final product.

Solid Forms

The various solid forms of Compound I can be prepared by dissolving Compound I in various suitable solvents and then causing Compound I to return to the solid phase. Specific combinations of solvents and conditions under which Compound I return to the solid phase are discussed in greater detail in the Examples.

A suitable solvent may solubilize Compound I, either partially or completely. Examples of suitable solvents useful in the present invention are a protic solvent, a polar aprotic solvent, or mixtures thereof. In certain embodiments, suitable solvents include an ether, an ester, an alcohol, or a mixture thereof. In certain embodiments, the suitable solvent is methanol, ethanol, propanol, dichloromethane, ethyl acetate, toluene, or tetrahydrofuran, wherein said solvent is anhydrous or in combination with water or hexane. In some embodiments, the suitable solvent is propanol in combination with water. In some embodiments, the suitable solvent is anhydrous ethanol. In some embodiments, the suitable solvent is toluene. In some embodiments, the suitable solvent is ethyl acetate in combination with hexane.

According to another embodiment, the present invention provides a method for preparing a solid form of Compound I, comprising the steps of dissolving Compound I with a suitable solvent and optionally heating to form a solution thereof; and isolating Compound I.

As described generally above, Compound I is dissolved in a suitable solvent, optionally with heating. In certain embodiments, Compound I is dissolved at about 40 to about 75° C. In some embodiments, Compound I is dissolved at about 70 to about 75° C. In some embodiments, Compound I is dissolved at the boiling temperature of the solvent. In other embodiments, Compound I is dissolved without heating (e.g., at ambient temperature, approximately 20-25° C.).

In certain embodiments, Compound I precipitates from the mixture. In another embodiment, Compound I crystallizes from the mixture. In other embodiments, Compound I crystallizes from solution following seeding of the solution (i.e., adding crystals of Compound I to the solution).

Crystalline Compound I can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent (e.g., water, hexane), by cooling (e.g., crash cooling) or by different combinations of these methods.

As described generally above, Compound I is optionally isolated. It will be appreciated that Compound I may be isolated by any suitable physical means known to one of ordinary skill in the art. In certain embodiments, precipitated solid Compound I is separated from the supernatant by filtration. In other embodiments, precipitated solid Compound I is separated from the supernatant by decanting the supernatant.

In certain embodiments, precipitated solid Compound I is separated from the supernatant by filtration.

In certain embodiments, isolated Compound I is dried in air. In other embodiments isolated Compound I is dried under reduced pressure, optionally at elevated temperature. Form 1 of Compound I is prepared according to the procedure described in Example 2 (see Step 5: Preparation of Compound I as Form 1).

Form 2 of Compound I is prepared according to the procedure described in Example 2 (see Preparation of Compound I as Form 2).

Uses, Formulation and Administration

In certain embodiments, compounds of the present invention are for use in medicine. In some embodiments, the present invention provides method of decreasing enzymatic activity of a kinase in the Tec kinase family (e.g., Tec, Btk, Itk, Txk, Lck, and Bmx). In some embodiments, such methods include contacting a kinase of the Tec kinase family with an effective amount of a Tec kinase family inhibitor. Therefore, the present invention further provides methods of inhibiting Tec kinase family enzymatic activity by contacting a Tec kinase family member with a Tec kinase family inhibitor of the present invention. As used herein, the term "Tec kinase family member" refers to any non-receptor tyrosine kinase in the Tec kinase family. In some embodiments, Tec kinase family members are Tec, Btk, Itk, Txk, Lck, and Bmx.

In some embodiments, the present invention provides methods of decreasing Btk enzymatic activity. In some embodiments, such methods include contacting Btk with an effective amount of a Btk inhibitor. Therefore, the present invention further provides methods of inhibiting Btk enzymatic activity by contacting a Btk with a Btk inhibitor of the present invention.

In some embodiments, inhibitors of such Tec kinases are useful for the treatment of diseases and disorders that may be alleviated by inhibiting (i.e., decreasing) enzymatic activity of one or more Tec kinases. The compounds of the invention are effective inhibitors of Tec family kinases and would thus be useful in treating diseases associated with the activity of one or more of the Tec family kinases. The term "diseases" means diseases, syndromes, or disease symptoms. Thus, the present invention provides methods of treating autoimmune disorders, inflammatory disorders, and cancers in a subject in need thereof. Such methods include administering to the subject a therapeutically effective amount of an inhibitor of Tec, Btk, Itk, Txk, Lck, and/or Bmx kinase.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), hemolytic anemia, autoimmune hepatitis, bullous pemphigoid (BP), Coeliac disease, dermatomyositis, diabetes mellitus type 1, Good Pasture's syndrome, Graves' disease, Guillain-Barré syndrome (GBS), Hashimoto's disease, idiopathic thrombocytopenic purpura, lupus or systemic lupus erythematosus (SLE), mixed connective tissue disease, multiple sclerosis, myasthenia gravis, pemphigus vulgaris, hemophilia with inhibitors, pernicious anaemia, polymyositis, primary biliary cirrhosis, Sjögren's syndrome, temporal arteritis, and Wegener's granulomatosis. The term "inflammatory disorders" includes diseases or disorders involving acute or chronic inflammation such as allergies, asthma (e.g., allergic asthma), atopic dermatitis, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection (including transplant patients with a positive cross-match) and vasculitis. In certain embodiments, the present invention provides methods of treating disease, disorders, or conditions that approved for treatment with rituximab (a monoclonal antibody against CD20), including non-Hodgkin's lymphoma (NHL), chronic lymphocytic leukemia (CLL), RA, Wegener's granulomatosis (WG), and microscopic polyangiitis (MPA). In some embodiments, the present invention provides a method of treating rheumatoid arthritis (RA), SLE, or atopic dermatitis using compounds disclosed herein.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

Selected Indications and B Cell Inhibition

As described above, Compound I is useful for the treatment of RA and SLE. As described in more detail below, these diseases are affiliated with B cells, and Compound I, as shown in the ensuing Examples, is an effective inhibitor of B cells. Thus, the present disclosure provides experimental evidence of Compound I as a therapeutic for these and other indications.

Dysregulation of the immune system is central to the pathogenesis (Panayi G S, et al. Rheum Dis Clin North Am 2001; 27:317-334) of RA. While most of the infiltrating leukocytes in the synovium are T lymphocytes (primarily activated CD4+ T cells) and cells of monocyte/macrophage origin (which release pro-inflammatory cytokines such as IL-1, TNF-alpha and IL-6 and proteolytic enzymes including collagenases and metalloproteinases), B-cells and plasma cells are also found in the synovial fluid (Zhang Z, Bridges S L. Rheum Dis Clin North Am 2001; 27:335-353). A clear role for B cells and their associated effector functions in RA have been demonstrated by the efficacy of rituximab, a selective B cell depleting therapeutic, which is approved for treatment of RA (Cohen S B, et al.; REFLEX Trial Group. Arthritis Rheum. 2006 September; 54(9):2793-806).

Although the etiology of SLE is not fully understood, pathogenic autoantibodies and deposition of immune complexes are felt to be critical to the development of widespread tissue damage (Klippel J H, et al. Primer on the rheumatic diseases. Atlanta: Arthritis Foundation; 2001). Autoantibody and immune-complex mediated activation can be studied by measuring inhibition of macrophage activation by macrophages stimulated through Fc receptors (see exemplification—FcγR activation of primary human macrophages). Loss of tolerance to self-antigens ultimately lead to the stimulation of B cells to produce auto-antibodies often directed against nuclear or cytoplasmic components. Antibodies against nuclear components (anti-nuclear antibodies [ANA]) target nuclear antigens including DNA (typically double-stranded DNA [dsDNA]), RNA, histones and small nuclear ribonucleoproteins. These antibodies combine with self-antigens forming immune complexes which deposit in tissues, incite inflammatory reactions and lead to tissue injury. In addition to their roles in pathogenic autoantibody production, B cells also function as antigen-presenting cells (APCs) to T-cells thus playing a role in the initiation of an antigen-specific response. Given the central role of the humoral arm of the immune system in the pathogenesis of SLE, B cells or the B-cell pathway represent desirable therapeutic targets. Belimumab a monoclonal antibody recently approved for SLE, blocks the binding BAFF to its receptors that are expressed B cells. These receptors serve to activate and potentiate the survival of B cells consistent with a reduction of circulating B cells observed following treatment with belimumab. See also Chan O T, et al. Immunol Rev. 1999b; 169:107-121; Navarra S V, et al. Lancet. 2011 Feb. 26; 377(9767):721-31; Furie R, et al. Arthritis Rheum. 2011 December; 63(12):3918-30. The role of B cells and myeloid lineage cells in autoimmune diseases such as SLE is further supported by a recent publication which describes efficacy in a preclinical SLE animal model when mice are treated with a small molecule irreversible Btk inhibitor (Honigberg, L. A. PNAS. 2010; 107: 13075).

Combinations

In certain embodiments, a compound or solid form of the present invention is administered in combination with another agent. In some embodiments, a compound or solid form of the present invention is useful for treating RA and is administered in combination with a disease-modifying anti-rheumatic drugs (DMARD), including without limitation: methotrexate, abatacept, azathioprine, certolizumab, chloroquine and hydroxychloroquine, cyclosporin, D-penicillamine, adalimumab, etanercept, golimumab, gold salts (including auranofin and sodium aurothiomalate), infliximab, leflunomide, minocycline, rituximab, sulfasalazine, tocilizumab, or combinations thereof. In some embodiments, a compound or solid form of the present invention is administered in combination with a NSAID or corticosteroid. In some embodiments, a compound or solid form of the present invention is useful for treating SLE and is administered in combination with an agent for the treatment of SLE, including without limitation: corticosteroids, antimalarials, belimumab, mycophenolate mofetil (MMF) or mycophenolate sodium, azathioprine, or combinations thereof. In some embodiments, a compound or solid form of the present invention is useful for treating atopic dermatitis and is administered in combination with a topical agent for the treatment of atopic dermatitis, including without limitation: topical steroids, tacrolimus, methotrexate, mometasone furoate (MMF), azathioprine, retinoids, or combinations thereof.

Assays

Compound I was tested in vitro and in vivo in Examples 8-16 described below. Compound I may also be found to decrease enzymatic activity of other Tec kinase family members. Tec kinases can be found in native cells, isolated in vitro, or co-expressed or expressed in a cell. Measuring the reduction in the Tec kinase family member enzymatic activity in the presence of an inhibitor relative to the activity in the absence of the inhibitor may be performed using a variety of methods known in the art, such as the POLYGAT-LS assays described below in the Examples. Other methods for assaying the activity of Btk and other Tec kinases are known in the art. The selection of appropriate assay methods is well within the capabilities of those of skill in the art.

Alternatively or additionally, Compound I may be tested for its ability to selectively inhibit a Tec kinase family member relative to other enzymes.

Compound I may be further tested in cell models or animal models for its ability to cause a detectable changes in phenotype related to a Tec kinase family member activity. In addition to cell cultures, animal models may be used to test Compound I for its ability to treat autoimmune disorders, inflammatory disorders, or cancer. Selected such models are described herein.

Pharmaceutical Compositions

In another aspect, the present invention provides pharmaceutical compositions comprising a Compound I or Compound I in combination with a pharmaceutically acceptable excipient (e.g., carrier).

The pharmaceutical compositions include optical isomers, diastereomers, or pharmaceutically acceptable salts of the inhibitors disclosed herein. Compound I included in the pharmaceutical composition may be covalently attached to a carrier moiety, as described above. Alternatively, Compound I included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be co-administered to the subject. Co-administration is meant to include simultaneous or sequential administration of the compounds individually or in combination (more than one compound). The preparations can also be combined, when desired, with other active substances (e.g. to reduce metabolic degradation).

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing kinase enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring kinase inhibition and adjusting the dosage upwards or downwards, as described above. In certain embodiments, the administered dose is in the range of about 10 mg to about 1000 mg per day, either once, twice, or more than twice daily.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

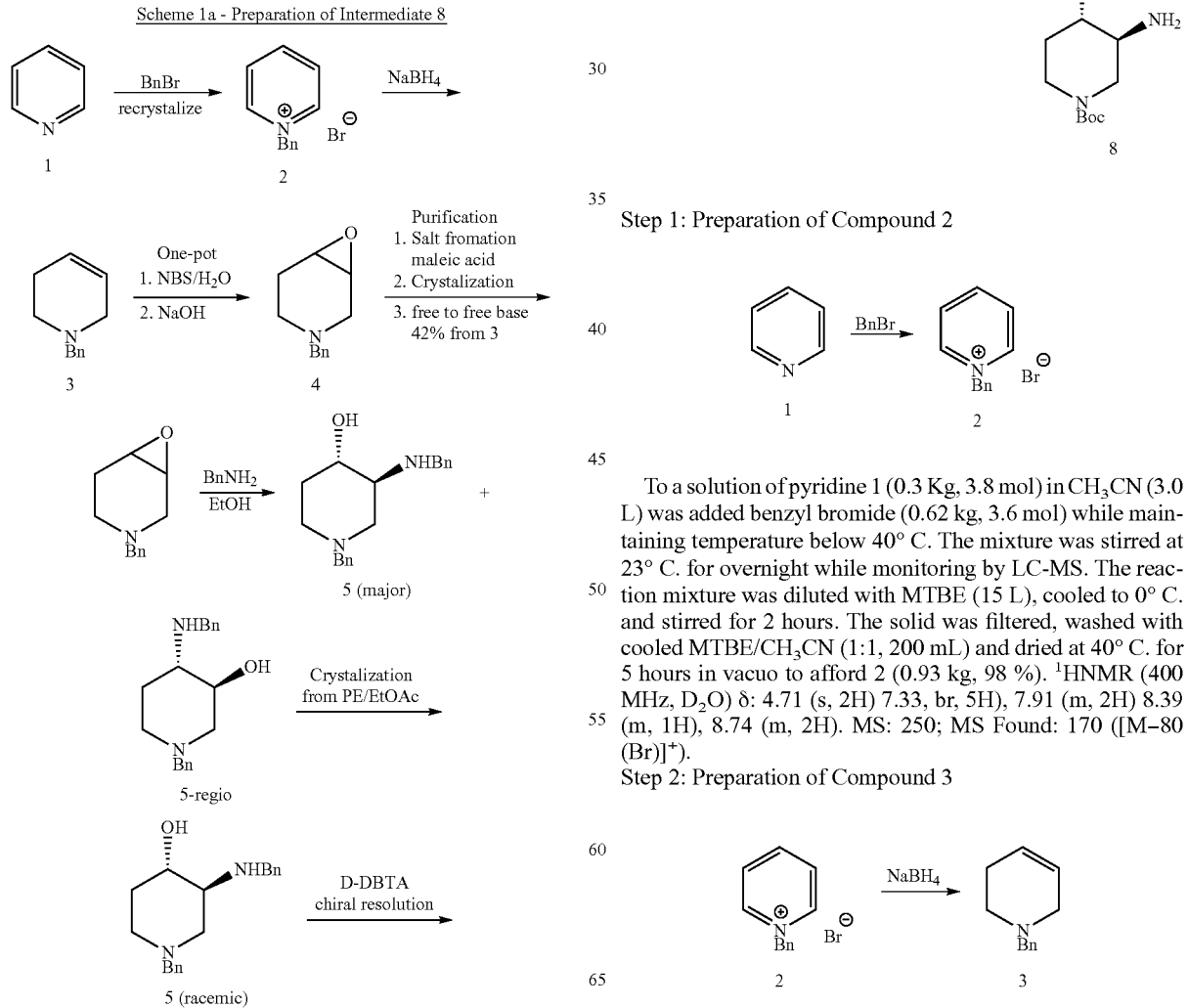

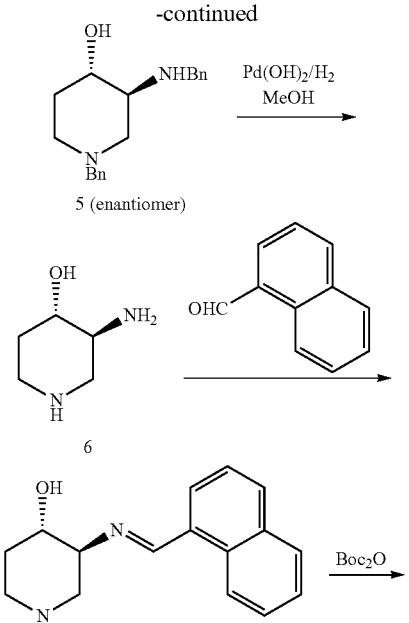

Step 1: Preparation of Compound 2

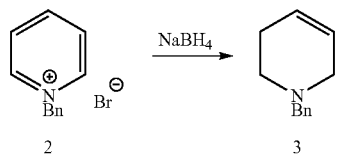

To a solution of pyridine 1 (0.3 Kg, 3.8 mol) in CH$_3$CN (3.0 L) was added benzyl bromide (0.62 kg, 3.6 mol) while maintaining temperature below 40° C. The mixture was stirred at 23° C. for overnight while monitoring by LC-MS. The reaction mixture was diluted with MTBE (15 L), cooled to 0° C. and stirred for 2 hours. The solid was filtered, washed with cooled MTBE/CH$_3$CN (1:1, 200 mL) and dried at 40° C. for 5 hours in vacuo to afford 2 (0.93 kg, 98 %). $^1$HNMR (400 MHz, D$_2$O) δ: 4.71 (s, 2H) 7.33, br, 5H), 7.91 (m, 2H) 8.39 (m, 1H), 8.74 (m, 2H). MS: 250; MS Found: 170 ([M−80 (Br)]$^+$).

Step 2: Preparation of Compound 3

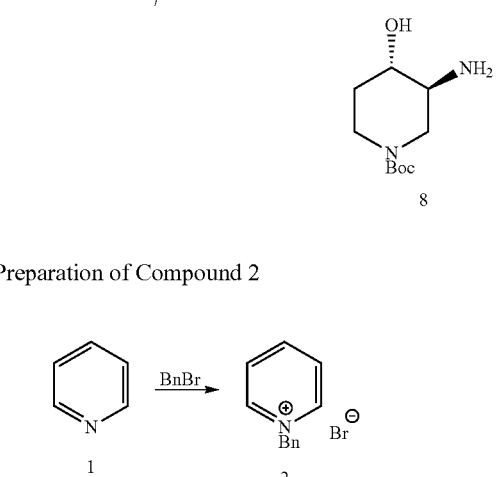

To a solution of compound 2 (0.91 kg, 3.6 mol) in MeOH (9.0 L) was added sodium borohydride (0.2 kg, 5.4 mol, 1.5 equiv) portion wise over 2 hours while maintaining reaction temperature<−5° C. The mixture was stirred for 1 hour at 20° C. The solvent was then removed at 45° C. in vacuo and the residue was diluted with EtOAc (5 L) and washed with saturated sodium carbonate solution (2 L) and brine (1 L). The aqueous phase was extracted with additional EtOAc (5 L) and the organic layers were combined, dried ($Na_2SO_4$), filtered and concentrated in vacuo to afford 3 as a crude product as an oil, (0.63 kg, 97.8%). The crude material was used directly in the next step without further purification. $^1$HNMR: ($CDCl_3$, 400 MHz) δ: 2.15-2.18 (m, 2H), 2.54-2.57 (m, 2H), 2.96-2.98 (m, 2H), 3.58 (s, 2H), 5.64-5.67 (m, 1H), 5.73-5.77 (m, 1H), 7.23-7.36 (m, 5H). MS: 174; MS Found: 175 ([M+1]$^+$).

Step 3: Preparation of Compound 4

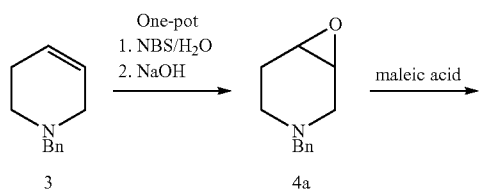

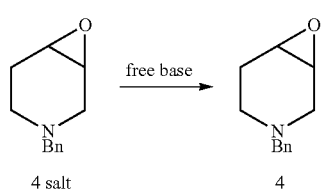

A mixture of TFA (0.43 kg, 3.81 mol) in water (6.3 L) was stirred at room temperature to which was added dropwise compound 3 (3.65 mol) and the resulting mixture was stirred at 20° C. for 1 hour. NBS (1.3 kg, 7.25 mol) was added portion wise, and the resulting mixture was warmed to 35° C. and stirred overnight. After cooling to 20° C., the reaction mixture was slowly added to a 20% NaOH solution (7 L), stirred overnight at 20° C. and the product was extracted with DCM (3×4 L). The combined organic layers were dried ($Na_2SO_4$), filtered and concentrated in vacuo to afford 4a (685.6 g) as a yellow oil. The crude 4a was added to a solution of maleic acid (417.8 g, 3.6 mol) in EtOH (6.6 L) and stirred for 48 hours to afford a slurry. The solid was filtered, washed with cold EtOH and dried at 45° C. in vacuo to afford 4 (471 g) as maleic acid salt. To a stirring solution maleic acid salt of 4 (431 g) was suspended in DCM (1.5 L) and water (0.6 L) was added 2 N NaOH solution (about 1 L) slowly until pH 9-10. The organic layer was separated and the aqueous layer was re-extracted with DCM (2×0.6 L). The combined organic layers were washed with brine (0.6 L), dried ($Na_2SO_4$) and concentrated in vacuo to give 4 (251.7 g) as a light brown oil (42% yield). $^1$HNMR (400.0 MHz, $CDCl_3$): δ2.00 (2 m, 2H), 2.18 (m, 1H), 2.29 (m, 1H), 2.66 (m, 1H), 2.97 (m, 1H), 3.18-3.24 (m, 2H), 3.40 (s, 2H), 6.98-7.24 (m, 5H); MS: 190; MS Found: 191 ([M+1]$^+$).

Step 4: Preparation of Compound 5

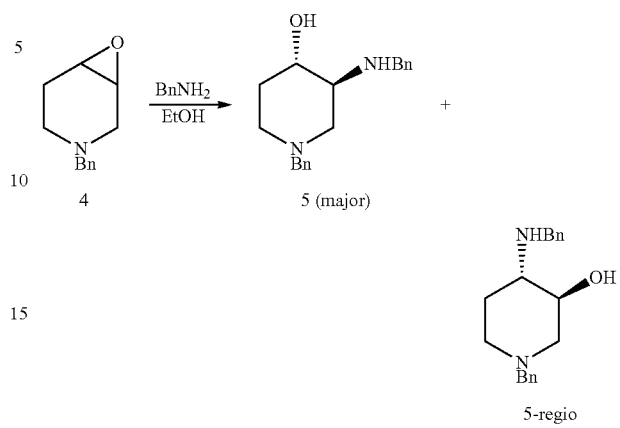

A mixture of 3-benzyl-7-oxa-3-azabicyclo[4.1.0]heptane 4 (250 g, 1.3 mol) and $BnNH_2$ (283 g, 2.6 mol) in EtOH (1.5 L) was stirred at room temperature and heated to reflux until LC-MS showed no starting material remaining. The mixture was cooled to 20° C. and diluted with water (7.5 L) and EtOAc (4 L). The aqueous layer was separated, extracted with EtOAc (3 L) and the combined EtOAc layers were dried ($Na_2SO_4$), filtered and concentrated in vacuo to give crude oil as a ~12:1 mixture of 5 and 5-regio isomers. The crude was crystallized from petroleum ether (1.5 L) and the solid was filtered, washed with petroleum ether (200 mL) and dried at 45° C. in vacuo to afford the desired product 5 (325 g, 83%) as a brown solid. $^1$HNMR (DMSO-d6, 400 MHz) δ: 1.36-1.44 (m, 1H), 1.70-1.75 (m, 2H), 1.93-1.98 (m, 1H), 2.13 (s, 1H), 2.36-2.42 (m, 1H), 2.63-2.66 (m, 1H), 2.91-2.93 (m, 1H), 3.13-3.19 (m, 1H), 3.44 (dd, 27.6, 13.2 Hz, 2H), 3.66 (dd, 40.8, 13.6 Hz, 2H), 4.73 (m, 1H), 7.19-7.33 (m, 10H). MS: 296; MS Found: 297 ([M+1]$^+$).

Step 5: Preparation of Compound 5D

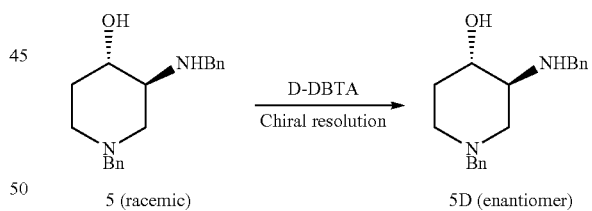

A mixture of 1-benzyl-3-(benzylamino)piperidin-4-ol 5 (171 g, 0.6 mol, 1.0 equiv) and D-DBTA (172.8 g, 0.5 mol, 0.8 equiv) was suspended in acetone:water (1:1, 5.1 L) and heated to reflux to obtain a clear solution. The mixture was cooled to 15-20° C. and the salt was precipitated out. Filtered and washed with of acetone: water (1:1, 50 mL) to afford the D-DBTA salt of 5. The salt was then suspended in DCM (500 ml) and water (100 mL) and stirred at room temperature, 2N NaOH was added until the pH>9 while maintaining the internal temperature<25° C. The product was extracted with additional DCM (2×200 mL). The combined organic layers were washed with brine (100 mL) and dried and concentrated to afford enantiomerically pure intermediate 5D (53.5 g, 31%) as white solid.

Step 6: Preparation of Compound 7

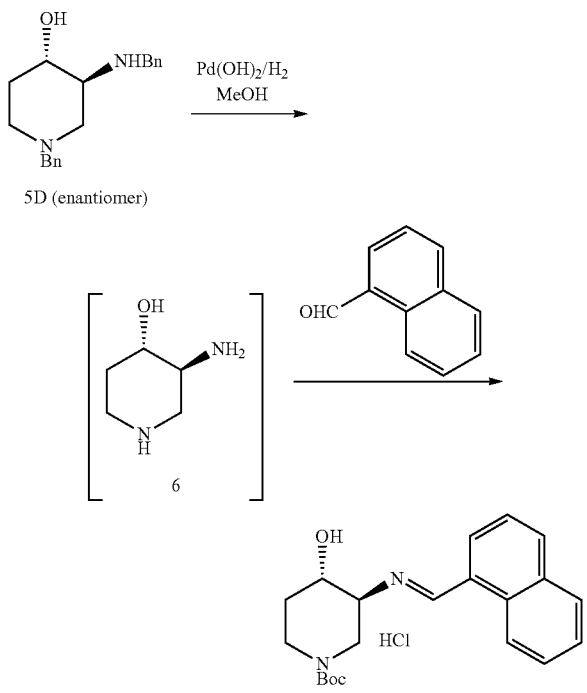

A mixture of (3R,4R)(benzylamino)piperidin-4-ol 5D (325 g, 1.09 mol), Pd(OH)$_2$ (130 g), HCl/EtOH (2 N, 5.0 mL) and MeOH (5.0 L) was stirred at 20° C. The mixture was stirred for 48 hours under 580 psi of hydrogen. The mixture was filtered and treated with 1-naphthaldehyde 6B (166.8 g, 1.07 mL) for 12 hours. The mixture was evaporated and the residue was suspended in MTBE (1 L) to afford a slurry, filtered and dried at 45° C. in vacuo to give afford 7 (267 g, 95% yield). $^1$H NMR (DMSO-d6, 400 MHz) δ: 1.73-1.76 (m, 1H), 2.05-2.09 (m, 1H), 3.03-3.12 (m, 2H), 3.26-3.30 (m, 2H), 3.45-3.47 (m, 1H), 3.66 (s, 1H), 5.28 (s, 1H), 7.57-7.62 (m, 2H), 7.96-8.04 (m, 4H), 8.26 (s, 1H), 8.54 (s, 1H), 9.15 (s, 2H). MS: 116; MS Found: 117 ([M+1]$^+$).

Step 7: Preparation of 8

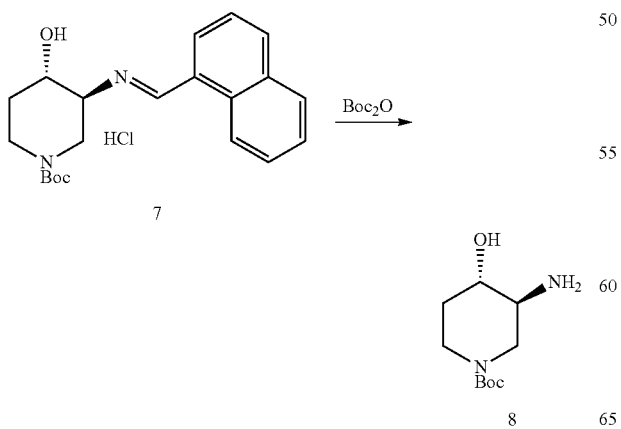

A mixture of (3R,4R)-3-((naphthalen-2-ylmethylene)amino)piperidin-4-ol hydrochloride 7 (267 g, 1.05 mol), Boc$_2$O (206 g, 0.94 mol), Et$_3$N (95.43 g, 0.95 mol) in THF (2.7 L) was stirred at room temperature for 4 hours until LC-MS showed complete consumption of starting material. The solution was adjusted to pH 2-3 with 1 N HCl and stirred overnight at 20° C. The solution was then adjusted to a pH 8-9 with saturated aqueous Na$_2$CO$_3$ and the mixture was stirred for 15 min at 20° C., the solvent was concentrated in vacuo and 1 N HCl was added to adjust pH 1-2, followed by extraction with DCM (1 L). The aqueous layer was basified with saturated Na$_2$CO$_3$ to pH 8-9 and extracted with DCM (3×1.2 L). The combined organic phases were dried over Na$_2$SO$_4$, filtered and concentrated in vacuo to afford a residue which was recrystallized in 20:1 petroleum ether/EtOAc (1 L) to afford a solid which was filtered, washed with petroleum ether (100 mL), dried at 45° C. in vacuo to afford 8 as a white solid (184 g, 81 yield). $^1$HNMR (D$_2$O, 400 MHz) δ: 1.31-1.39 (m, 10H), 1.83-1.87 (m, 1H), 2.47-2.59 (m, 2H), 2.81-2.87 (m, 1H), 3.33-3.39 (m, 1H), 3.90-3.92 (m, 2H). MS: 216; MS Found: 161, 117 217([M−56+1]$^+$, [M−100+1]$^+$, [M+1]$^+$), optical rotation: −15.6 c=1, MeOH; >99% ee by chiral HPLC.

In some embodiments, the enantiomer of intermediate 8 is prepared according to Scheme 1b.

Scheme1b - Alternate Synthesis of Enantiomer of Intermediate 8

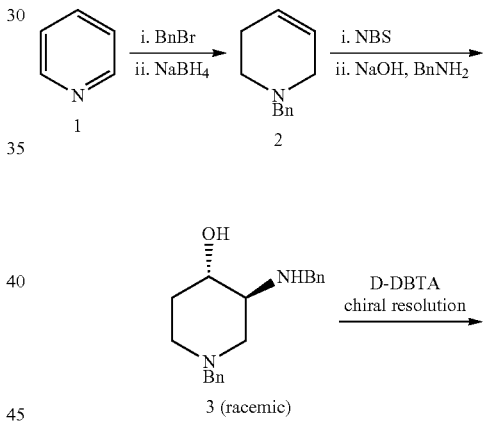

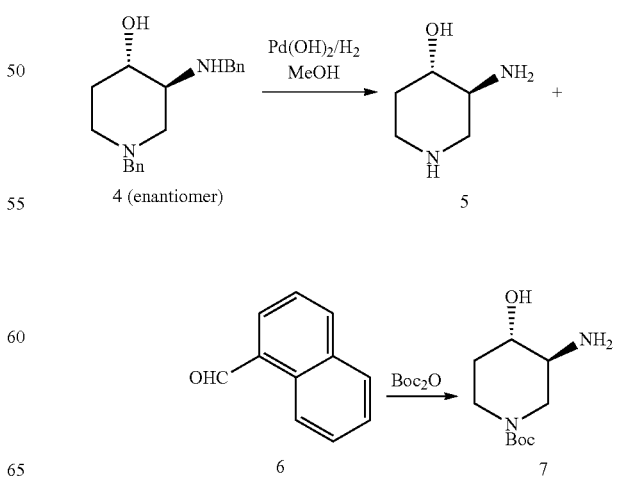

Example 2

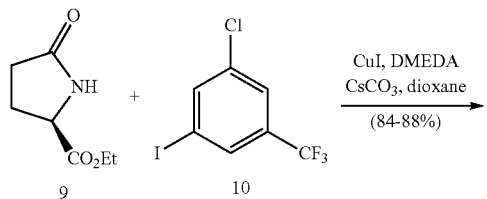

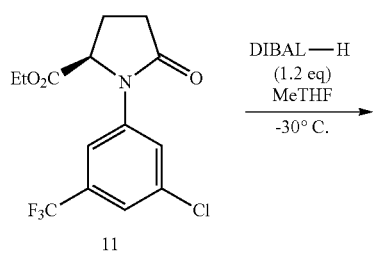

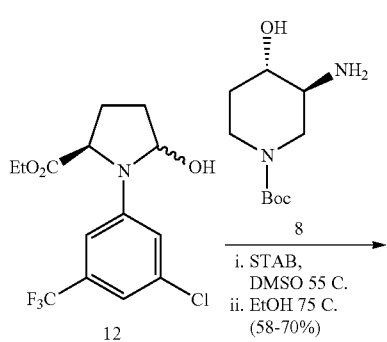

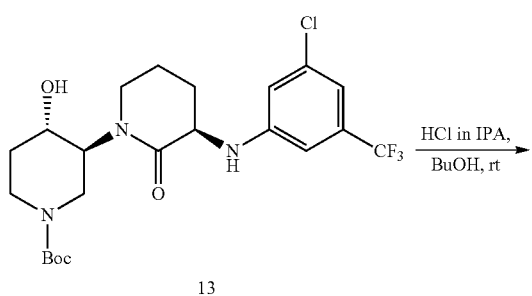

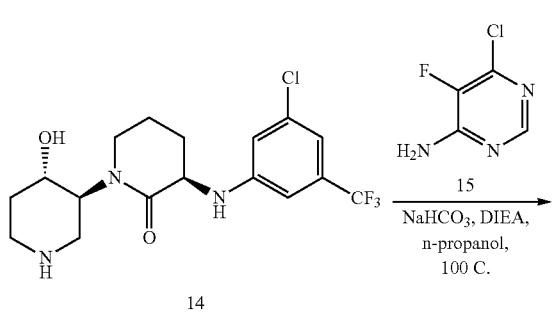

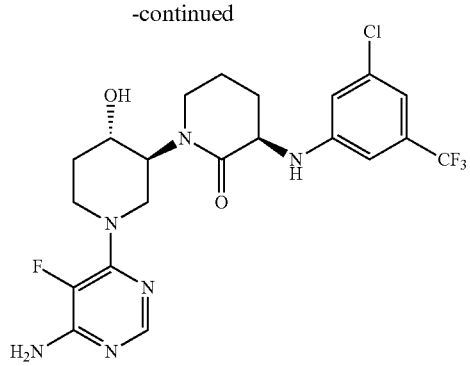

Step 1: Preparation of 11

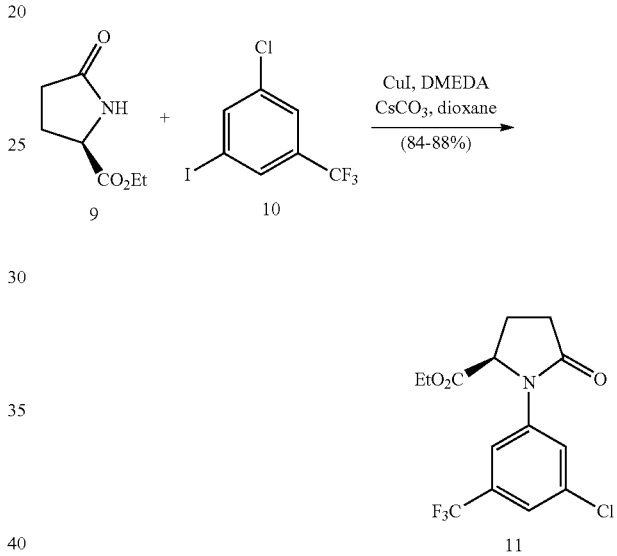

A mixture of 1-chloro-3-iodo-5-(trifluoromethyl)benzene (150 g, 489 mmol), (R)-ethyl 5-oxopyrrolidine-2-carboxylate (108 g, 683 mmol), copper (I) iodide (23.3 g, 122 mmol), CsCO₃ in 1,4-dioxane (1 L) was stirred under an atmosphere of nitrogen followed by the addition of N,N'-diemthyl-1,2-ethanediamine (26 mL, 245 mmol). The mixture was heated to 40° C. for 4 hours, followed by the addition of copper (I) iodide (11.4 g, 60 mmol) and N,N'-diemthyl-1,2-ethanediamine (13 mL, 123 mmol) and heating at 40° C. was continued overnight. The was diluted with water (600 mL) and saturated aqueous $NH_3$ and MTBE (600 mL) and the mixture was stirred for 10 min and allowed to separate into two distinct layers. The aqueous layer was separated and extracted with MBTE (2×300 mL) and the combined organic layers were washed sequentially with a mixture of water (150 mL)/saturated brine (15 mL), followed by 2 N HCl (300 mL) and then water (230 mL). The organic phase was dried over $Na_2SO_4$, filtered and concentrated in vacuo to afford 10 as an oil. ¹H NMR (400 MHz, CHLOROFORM-d) δ: 7.85 (t, J=2.13 Hz, 1H), 7.63 (t, J=2.01 Hz, 1H), 7.41 (t, J=1.88 Hz, 1H), 4.73 (dd, J=2.89, 8.91 Hz, 1H), 4.18-4.29 (m, 2H), 2.73-2.83 (m, 1H), 2.57-2.65 (m, 1H), 2.49-2.55 (m, 1H), 2.19-2.31 (m, 1H), 1.68 (s, 1H), 1.22-1.32 (m, 3H). MS: 335; MS Found: 335.9 ([M+1]⁺.

Step 2: Preparation of 12

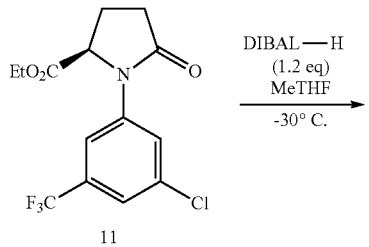

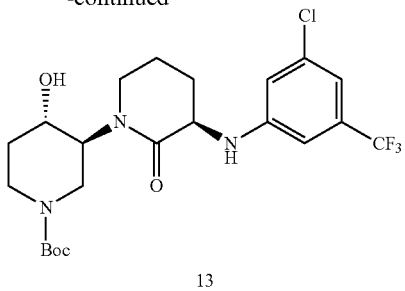

To a solution of anhydrous 2-methyl-THF (500 mL, KF<200 ppm) was added ethyl 1-(3-chloro-5-(trifluoromethyl)phenyl)-5-oxopyrrolidine-2-carboxylate (52 g, 154 mmol) and allowed to stir for 15 min under an atmosphere of nitrogen. The solution was cooled to −35 to −45° C. to which was a solution of DIBAL (1 N in heptane, 169 mL, 169 mmol) at a rate that maintained an internal solution temperature of −35 to −45° C. The reaction was monitored by HPLC (C18 reverse phase Kenetex 150 mm×4.6 mm, 2.6 um, mobile phase gradient $CH_3CN$/water/TFA 0.1%, 243 nm). The reaction was quenched with an aqueous solution of Rochelle salt (1 M, 400 mL) at −35° C. and the mixture was then heated to 35° C., stirring was stop and the aqueous phase was separated. The organic layer was washed two additional times with aqueous solution of Rochelle salt (1 M, 400 mL) following the above protocol. To the organic solution was added triethylamine (25 mL, 50% v/w) and the solvent was removed in vacuo to afford 12 as a clear oil.

Step 3: Preparation of 13

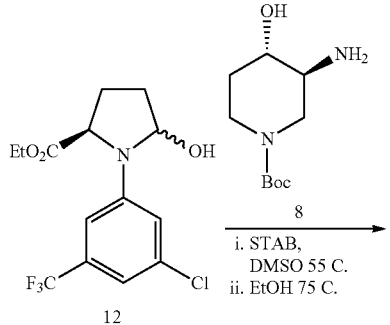

To a solution of (2R)-ethyl 1-(3-chloro-5-(trifluoromethyl)phenyl)-5-hydroxypyrrolidine-2-carboxylate (37 g, 110 mmol) in DMSO (370 mL) was added (3S,4S)-tert-butyl 3-amino-4-hydroxypiperidine-1-carboxylate (26 g, 120 mmol) and heated to 45° C. with stirring under atmosphere of nitrogen until a clear solution was formed. To the solution was added sodium triacetoxy borohydride (58 g, 275 mmol) and heated to 55° C. for 2 h. The reaction was monitored by HPLC (C18 reverse phase Kenetex 150 mm×4.6 mm, 2.6 um, mobile phase gradient $CH_3CN$/water/TFA 0.1%, 243 nm). Upon complete consumption of (2R)-ethyl 1-(3-chloro-5-(trifluoromethyl)phenyl)-5-hydroxypyrrolidine-2-carboxylate 12, ethanol (19 mL, 50% v/w) was added to the reaction and the solution was stirred for 15-30 min at 55° C. The mixture was heated to 75° C. while monitoring by HPLC (C18 reverse phase Kenetex 150 mm×4.6 mm, 2.6 um, mobile phase gradient $CH_3CN$/water/TFA 0.1%, 243 nm). Upon completion formation of product, the reaction was cooled to rt and diluted with EtOAc (370 mL), water (370 mL) and stirred for 15 min. The organic phase was separated and washed with a 25% solution of brine (185 mL×3) and the organic phase was concentrated in vacuo to afford 13 as a waxy solid. The crude material was recrystallized from EtOAc/heptane to afford the desired product as a white crystal. $^1$H NMR (400 MHz, DMSO-$d_6$) δ: 6.93 (s, 2H), 6.81 (s, 1H), 6.57 (d, J=7.78 Hz, 1H), 4.87 (d, J=5.27 Hz, 1H), 4.14 (td, J=7.22, 9.91 Hz, 1H), 3.81-3.98 (m, 2H), 3.71 (dt, J=4.89, 10.10 Hz, 2H), 3.35-3.45 (m, 1H), 2.13 (dd, J=6.27, 12.55 Hz, 1H), 1.83-1.95 (m, 2H), 1.78 (dd, J=6.53, 12.80 Hz, 1H), 1.56 (d, 1=10.79 Hz, 1H), 1.38 (s, 10H), 1.20-1.35 (m, 1H).

Step 4: Preparation of 14

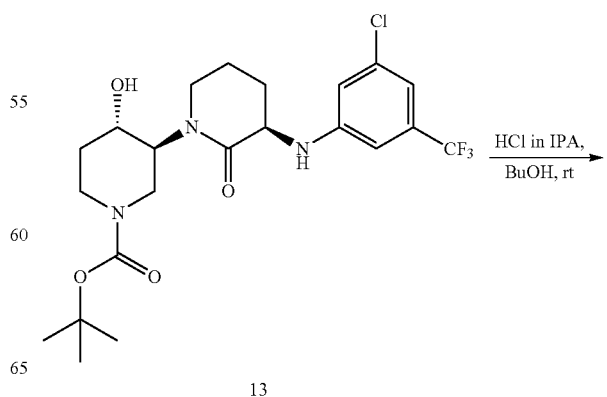

-continued

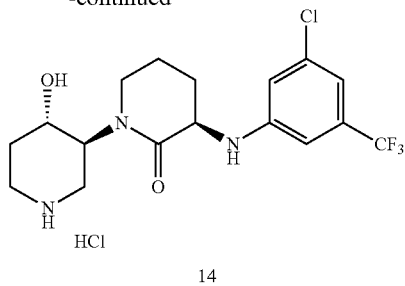

14

To a slurry of (3R,3'S,4'S)-tert-butyl 3-((3-chloro-5-(trifluoromethyl)phenyl)amino)-4'-hydroxy-2-oxo-[1,3'-bipiperidine]-1'-carboxylate (25.5 g, 46.6 mmol) and 1-butanol (120 mL) was added HCl in isopropanol solution (4.8 M, 73 mL, 7.6 equiv). The mixture was stirred at room temperature for 17 h. Water (2.0 g, ~2.4 equiv) was added to the reaction and the mixture was stirred at room temperature for 30 min, cooled in an ice bath for 2 h and filtered in vacuo. The filter cake was washed with IPA (2×15 mL) and dried on the funnel in vacuo at 22° C. overnight and then under high vacuum at 40° C. for 4 h to afford 14 (20.5 g). $^1$H NMR (400 MHz, DMSO-d$_6$) δ 9.64 (d, J=9.54 Hz, 1H), 9.06 (d, J=7.03 Hz, 1H), 6.88-6.99 (m, 2H), 6.71-6.84 (m, 1H), 4.25 (br. s., 1H), 4.16 (dd, J=6.40, 9.91 Hz, 1H), 3.86 (dt, J=4.77, 10.42 Hz, 1H), 3.30-3.41 (m, 1H), 3.20 (d, J=12.55 Hz, 1H), 2.97-3.10 (m, 2H), 2.88 (d, J=11.04 Hz, 1H), 2.07-2.19 (m, 1H), 2.02 (d, J=10.54 Hz, 1H), 1.73-1.96 (m, 2H), 1.52-1.73 (m, 2H), 1.25-1.41 (m, 1H).

Step 5: Preparation of Compound I as Form 1

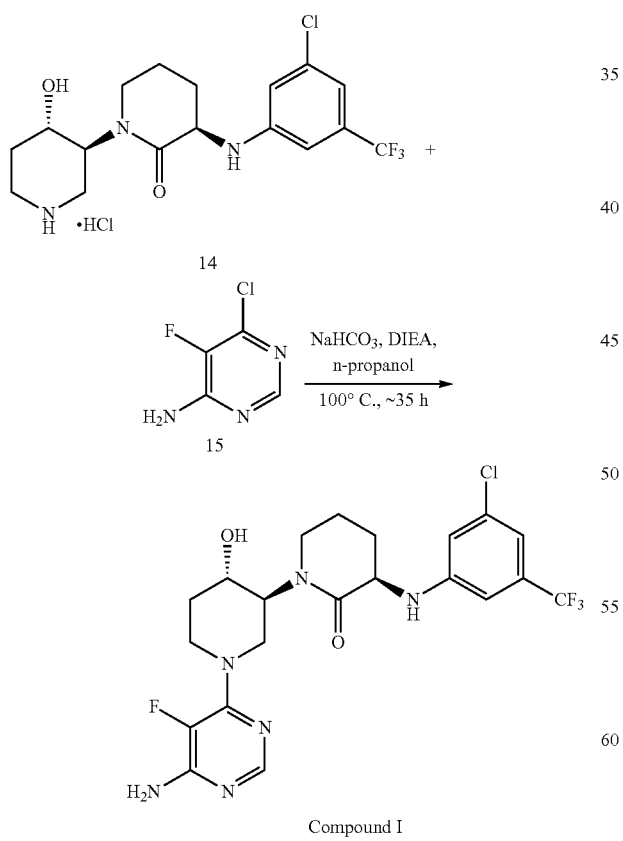

To a solution of 6-chloro-5-fluoro-pyrimidin-4-ylamine 14 (59.2 g, 0.40 mol) in 1-propanol (400 mL) was added (3R, 3'S,4'S)-3-((3-chloro-5-(trifluoromethyl)phenyl)amino)-4'-hydroxy-[1,3'-bipiperidin]-2-one hydrochloride (200 g, 0.47 mol), NaHCO$_3$ (67.4 g, 0.8 mol) in 3-5 portions followed by addition of DIEA (60.5 g, 84 mL, 0.47 mol). The suspension was heated at 100° C. for 36 h and diluted by the addition of H$_2$O (400 mL) and stirred at 70-85° C. for 5 min to dissolve the solid. The mixture was allowed to form two layers, the bottom aqueous layer was removed. The organic phase was diluted with propanol (300 mL) and heated the mixture to 70-75° C. followed by addition of H$_2$O (300 mL) dropwise over 25-30 min keeping internal temperature 70-75° C. The mixture was cooled to 49° C. and seeds of compound I were added when the internal temperature reached 51 to 49° C. and stirred at 42-49° C. for 1.5 h, when a good seeds bed formed. To the mixture was added H$_2$O (810 mL) over 60-80 min maintaining internal temperature 46-49° C. The mixture was then cooled 0° C. in 1.5 h, filtered and the filter cake was washed with H$_2$O (300 mL), dried in vacuo overnight and further dried in vacuum oven at 40° C./15 mbar for 2 h to afford compound I as a crystal solid form 1 (160.2 g, 79.3% yield). $^1$H NMR (CDCl$_3$, 500 MHz) δ 7.92 (s, 1H), 6.91 (s, 1H), 6.73 (d, J=1.8 Hz, 1H), 6.71 (t, J=2.0 Hz, 1H), 5.27 (d, J=4.2 Hz, 1H), 4.87 (s, 2H), 4.43-4.37 (m, 2H), 4.14-4.00 (m, 2H), 3.92 (ddd, J=11.4, 5.8, 3.8 Hz, 1H), 3.51 (dt, J=11.6, 6.0 Hz, 1H), 3.40 (dt, J=12.9, 6.6 Hz, 1H), 3.10 (dd, J=12.8, 10.7 Hz, 1H), 2.92 (td, J=13.3, 2.5 Hz, 1H), 2.45 (dq, J=11.7, 5.7 Hz, 1H), 2.17-2.09 (m, 1H), 2.08-1.94 (m, 2H), 1.71-1.55 (m, 2H). $^{13}$C NMR (CDCl$_3$, 126 MHz) δ 171.4, 152.5 (d, J$_{C-F}$=11.8 Hz), 151.9 (d, J$_{C-F}$=10.0 Hz), 149.4, 148.5, 135.5, 132.7 (q, J$_{C-F}$=33.2 Hz), 132.5 (d, J$_{C-F}$=248.7 Hz), 123.5 (q, J$_{C-F}$=247.6 Hz), 115.6, 114.1 (d, J=4.1 Hz), 108.2, 69.0, 59.6, 53.6, 46.4, 45.2, 43.5, 34.3, 26.3, 20.6. $^{19}$F NMR (CDCl$_3$, 376 MHz) δ −63.2 (s, 3F), −164.2 (s, 1F).

Preparation of Compound I as Form 2

To a 20 mL flask was added 220 mg (0.437 mmol) of amorphous Compound I and 11 mL of toluene. The flask was heated to 60° C. and stirred until Compound I was completely dissolved. Cooling the sample to room temperature resulted in the precipitation of a clear gel. The gel was re-dissolved by heating to 60° C. and the flask was immediately placed in a refrigerator set to 5° C. After incubating overnight a crystalline precipitate was observed. The precipitate was isolated by filtration, washed with cold toluene and dried in a vacuum oven at 60° C. for 2 hours. PXRD of the solids confirmed the presence of Compound I as crystalline form 2.

In some embodiments, Compound I is prepared according to Scheme 2a or 2b.

Scheme 2a - Alternate Synthesis of Compound I

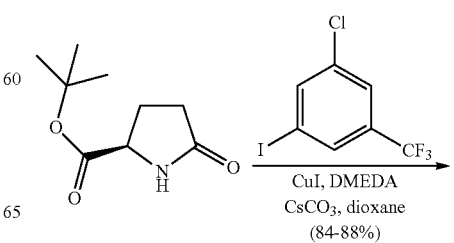

33
-continued
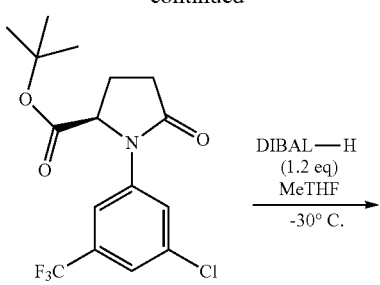
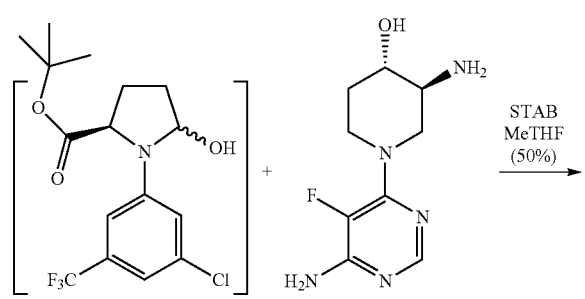
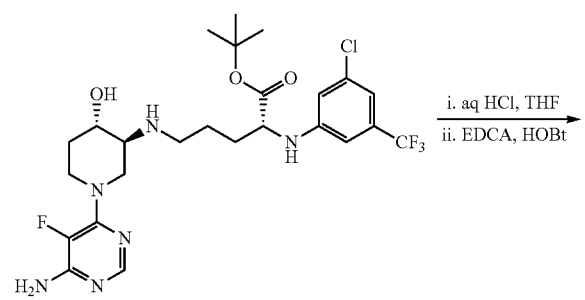
Scheme 2b - Alternate Synthesis of Compound I
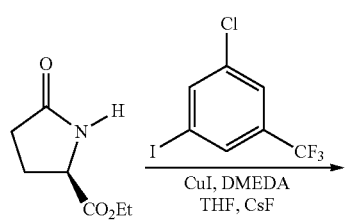
34
-continued
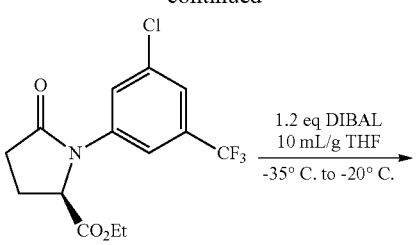
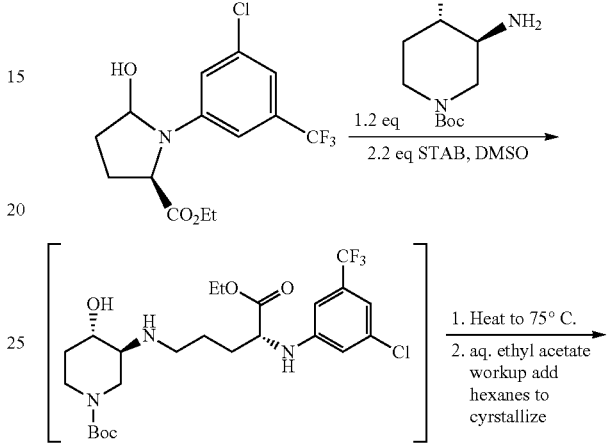
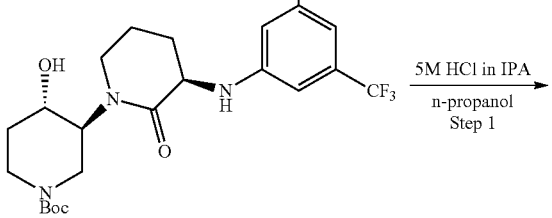
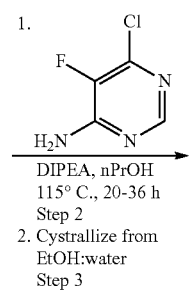
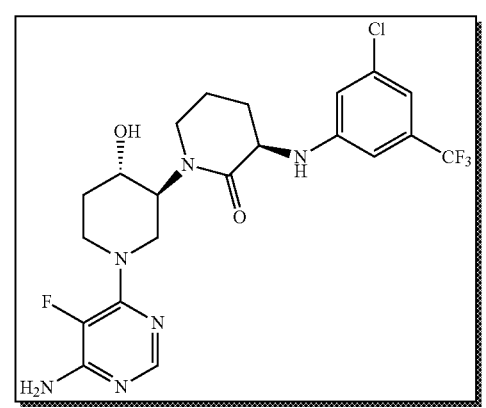

Example 3

Scheme III - Preparation of Compound 17

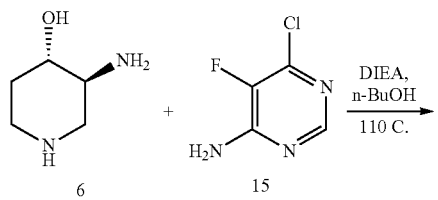

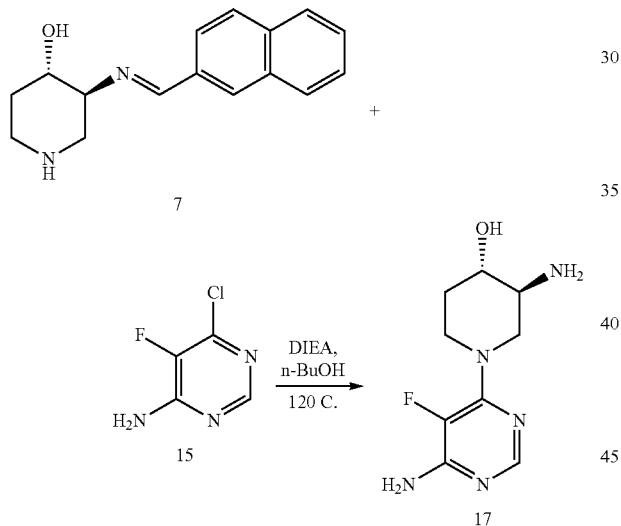

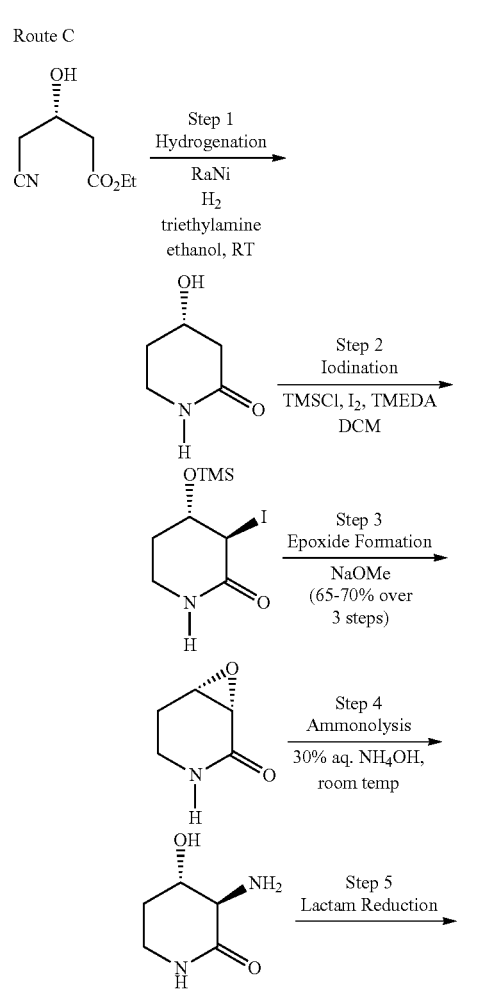

Route A

To a solution of (3S,4S)-3-aminopiperidin-4-ol 6 (9.4 g, 81.0 mmol, 1.0 equiv) in n-BuOH (100 ml) was added 6-chloro-5-fluoro-pyrimidin-4-ylamine (11.3 g, 76.9 mmol, 0.95 equiv) and the mixture was heated to 120° C. overnight. The solid crystallized upon cooling to 20° C. After stirred for 2 h, the mixture was filtered and the solids were washed with MTBE (100 ml), dry under vacuum at 50° C. (−0.08 Mpa) for ~4-5 hours to afford 17 as a gray solid (17 g, 79.8%). $^1$H NMR (DMSO-d6, 400 MHz) δ: 1.40-1.45 (m, 1H), 1.93 (m, 1H), 2.60-2.69 (m, 2H), 2.90 (t, J=12.0 Hz, 1H), 3.41-3.47 (m, 1H), 3.93-4.01 (m, 2H), 7.59 (s, 1H). MS: 227; MS Found: 228 ([M+1]$^+$).

Route B

To a solution of (3S,4S)-3-((naphthalen-2-ylmethylene) amino)piperidin-4-ol (522 g, 1.8 mol, 1.0 equiv) in n-BuOH (10 L) was added DIPEA (580 g, 4.5 mol, 2.5 equiv), 6-chloro-5-fluoro-pyrimidin-4-ylamine (265 g, 1.8 mol, 1.0 equiv) and the mixture was heated to 110° C. for 72 h. The solution was cooled to room temperature and quenched with 3 N HCl to adjust pH to ~2-3, the aqueous layer was separated, washed with DCM (1 L) and treated with 4 L of acidic exchanged resin (Type 732) overnight. The resin collected by filtration and eluted with 3 N NH$_3$ MeOH solution (15 L). The eluent was concentrated to about 500 mL to give a slurry mixture. The solids were collected by filtration and washed with water, dried at 50° C. in vacuo to afford 304 g of compound 17 (75% yield) as light brown solid.

In some embodiments, compound 17 is prepared according to Route C.

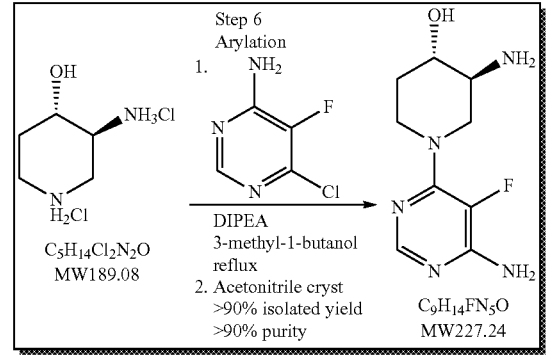

In some embodiments, a salt form of compound 17 is prepared according to Route D, which may be transformed to Compound I as further shown below.

Route D

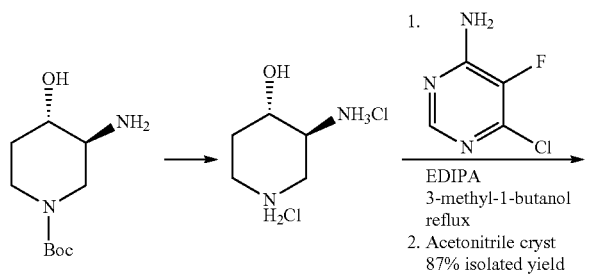

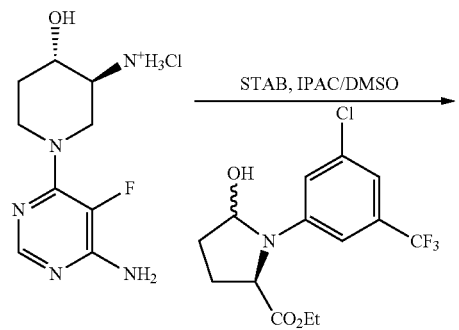

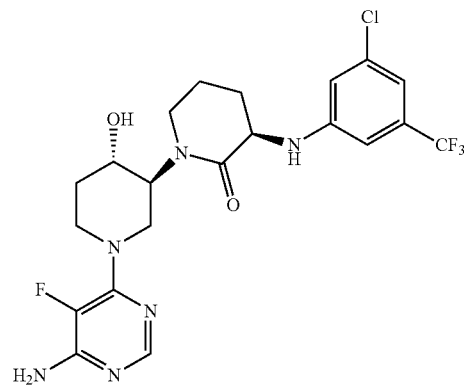

Example 4

Scheme IV

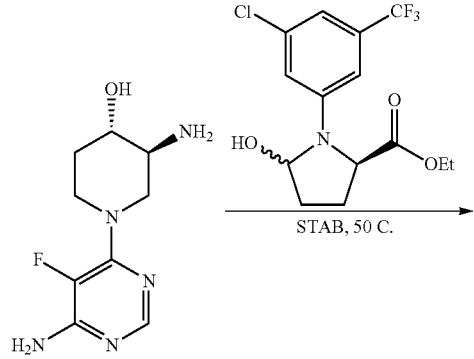

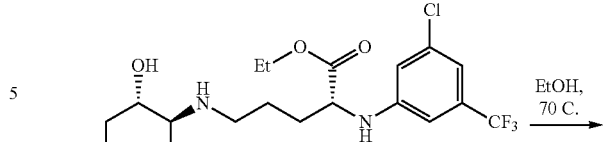

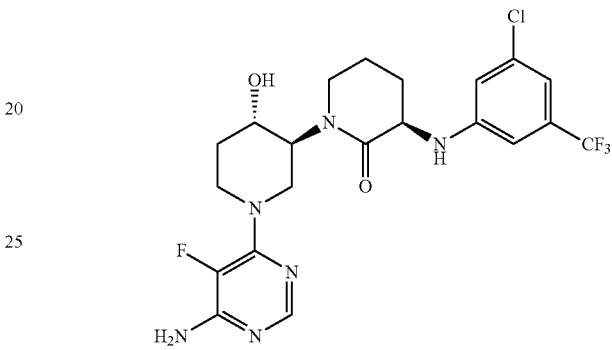

(2R)-Ethyl-1-(3-chloro-5-(trifluoromethyl)phenyl)-5-hydroxypyrrolidine-2-carboxylate (5.3 g, 16.6 mmol, 1.0 equiv), (3S,4S)(6-amino-5-fluoropyrimidin-4-yl)piperidin-4-ol (4.2 g, 18.5 mmol, 1.1 equiv) and sodium triacetoxyborohydride (7.8 g, 36.8 mmol, 2.0 equiv) were mixed in DMSO (56 ml) at 20° C. The mixture was heated to 50° C. for 2 hours while monitoring by HPLC (C18 reverse phase Kenetex 150 mm×4.6 mm, 2.6 um, mobile phase gradient $CH_3CN$/water/ TFA 0.1%, 243 nm). Upon complete consumption of (2R)-ethyl 1-(3-chloro-5-(trifluoromethyl)phenyl)-5-hydroxypyrrolidine-2-carboxylate 12 ethanol (19 mL, 50% v/w) EtOH (2.8 mL) was then added to and after 20 min, the mixture was heated to 75° C. with stirring overnight. The reaction mixture was quenched with water (400 mL) and extracted with DCM (200 mL×2). The combined organic layers were washed with water (100 mL×2), sat.$K_2CO_3$, (100 mL), brine (100 mL), dried ($Na_2SO_4$), filtered and concentrated in vacuo to afford a crude product. The crude was recrystallized from EtOAc/hexane (12 mL/12 mL) to afford 16 (3.45 g, 47%) as an off-white solid. $^1$HNMR (DMSO-d6, 400 MHz) δ: 1.41-1.51 (m, 1H), 1.51-1.62 (m, 1H), 1.76-1.82 (m, 1H), 1.88-1.99 (m, 2H), 2.10-2.17 (m, 1H), 2.83-2.99 (m, 2H), 3.30-3.34 (m, 1H), 3.40-3.46 (m, 1H), 3.80-3.81 (m, 1H), 4.02-4.09 (m, 2H), 4.14-4.20 (m, 2H), 4.88 (s, 1H), 6.58-6.62 (m, 3H), 6.80 (s, 1H), 6.95 (s, 1H), 7.76 (s, 1H); MS: 502; MS Found: 503 ([M+1]$^+$).

Example 5

Alternative synthesis of Compound I. In addition to the routes described above, Compound I was also synthesized according to Scheme B.

Scheme B
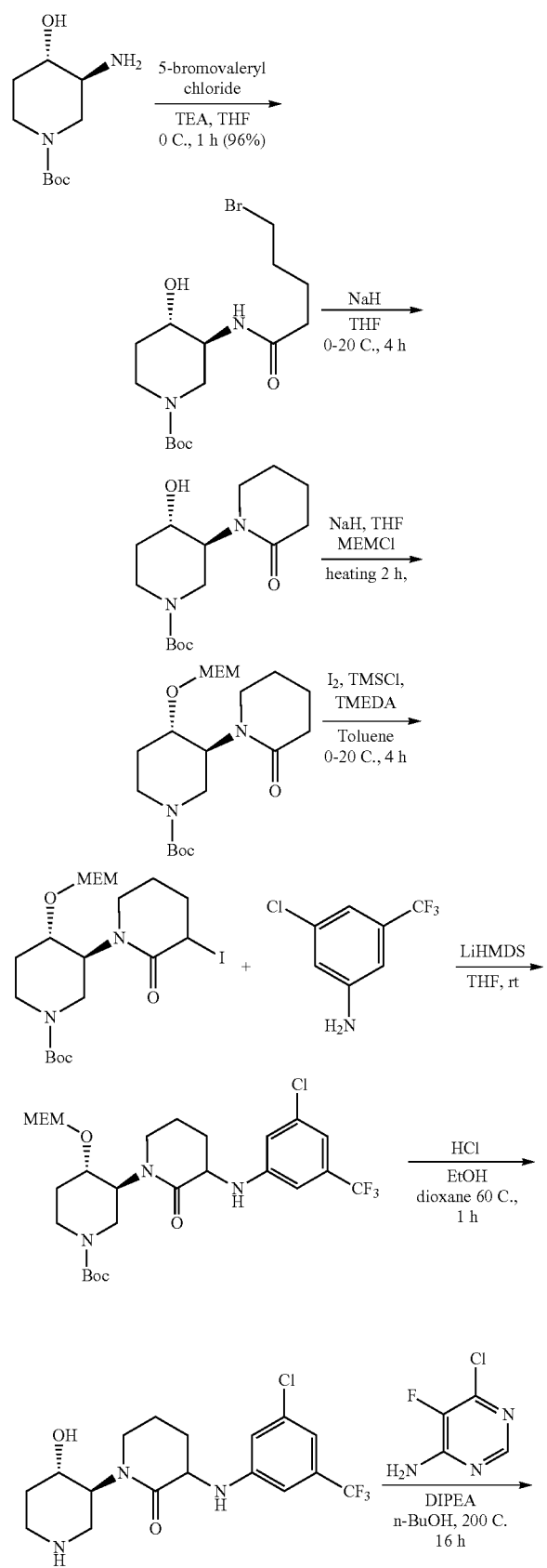
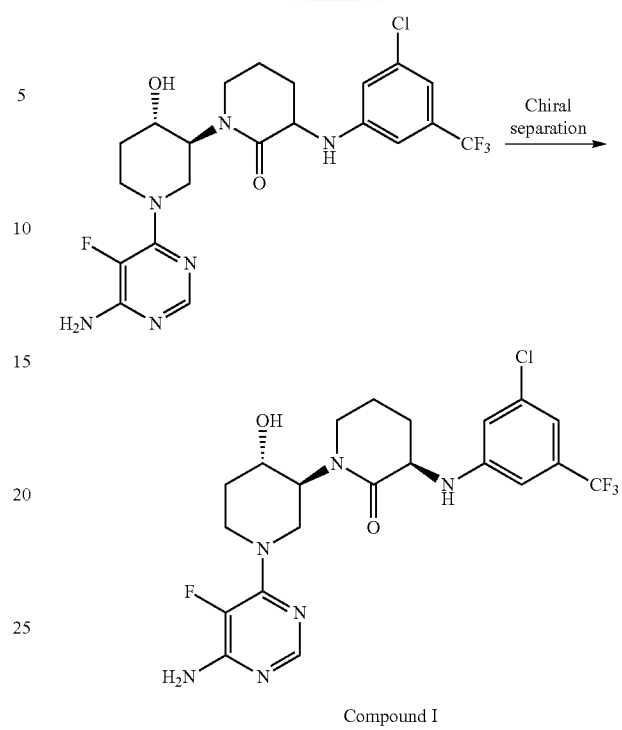
Compound I
Example 6
Stable label of Compound I. A radiolabelled analog of Compound I may be made according to the procedure set forth in Scheme C.
Scheme 6
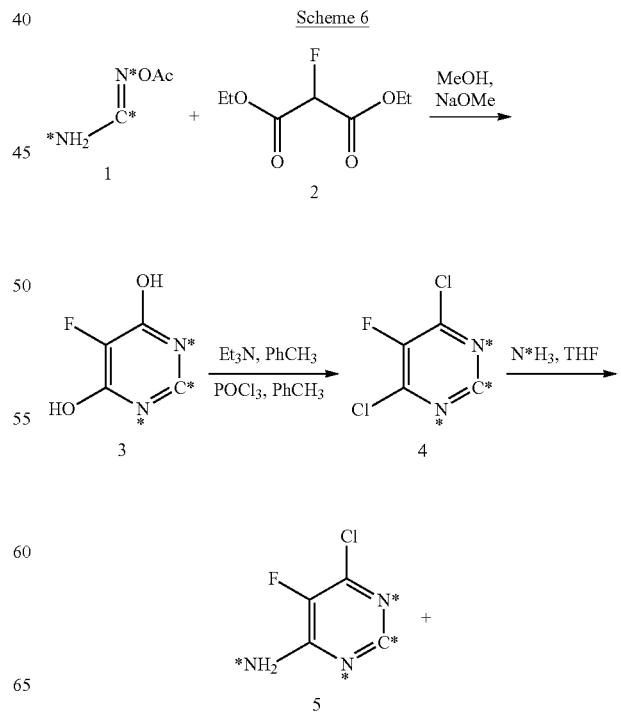

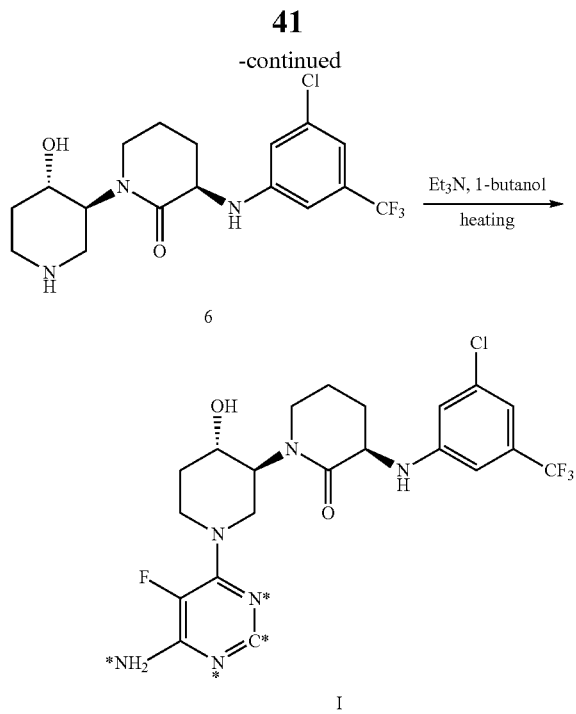

Example 7

Additional Characterization of Compound I

Powder X-Ray Diffraction (PXRD)

Crystallinity was studied with a Bruker-D8 Advance X-ray powder diffractometer using Cu Ka radiation (Bruker, Madison, Wis.). The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a Lynxeye detector. A θ-2θ continuous scan from 3 to 39° 2θ with 0.016°/min steps and a 0.5 sec/step dwell time was used. Samples were prepared for analysis by placing them on a zero background plate. See FIG. 1.

Dynamic Vapor Sorption (DVS)

DVS analysis was performed on Form 1 of Compound I using a VTI SGS-CX3 DVS (TA Instruments, New Castle, Del.). 10-20 mg of sample was dried at 40° C./0% relative humidity (RH) for 2 hours prior to the start of the run. Samples were then held isothermal at 25° C. and equilibrated at increasing and decreasing RH conditions from 5-90-5% RH for two cycles. The equilibrium criterion was set to 0.02 weight percent in five minutes with a maximum equilibration time of 120 minutes. No appreciable absorption of water from 5-50% relative humidity (RH). See FIG. 2.

Differential Scanning Calorimetry (DSC)

DSC was performed using a Perkin Elmer Diamond DSC (Waltham, Mass.). 0.5-1.5 mg of sample was placed in a crimp sealed aluminum pan and heated with a linear gradient from 30° C.-300° C. at 10° C. per minute. See FIG. 3.

Example 8

In vitro BTK kinase assay: BTK-POLYGAT-LS ASSAY. The purpose of the BTK in vitro assay was to determine compound potency against BTK through the measurement of $IC_{50}$. Compound inhibition was measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 uL aliquot of an ATP/peptide master mix (final concentration; ATP 10 uM, polyGAT 100 nM) in kinase buffer (10 mM Tris-HCl pH 7.5, 10 mM $MgCl_2$, 200 uM $Na_3PO_4$, 5 mM DTT, 0.01% Triton X-100, and 0.2 mg/ml casein) was added to each well. Next, 1 uL of a 4-fold, 40× compound titration in 100% DMSO solvent was added, followed by adding 15 uL of BTK enzyme mix in 1× kinase buffer (with a final concentration of 0.25 nM). The assay was incubated for 30 minutes before being stopped with 28 uL of a 50 mM EDTA solution. Aliquots (5 uL) of the kinase reaction were transferred to a low volume white 384 well plate (Corning 3674), and 5 uL of a 2× detection buffer (Invitrogen PV3574, with 4 nM Tb—PY20 antibody, Invitrogen PV3552) was added. The plate was covered and incubated for 45 minutes at room temperature. Time resolved fluorescence (TRF) on Molecular Devices M5 (332 nm excitation; 488 nm emission; 518 nm fluorescein emission) was measured. $IC_{50}$ values were calculated using a four parameter fit with 100% enzyme activity determined from the DMSO control and 0% activity from the EDTA control.

Compound I was found to be active in the polyGAT assay, with an $IC_{50}$ value of 1.97 nM. Comparator compounds $I^{C1}$ and $I^{C2}$, shown below, each produced $IC_{50}$ values of 2.0 nM.

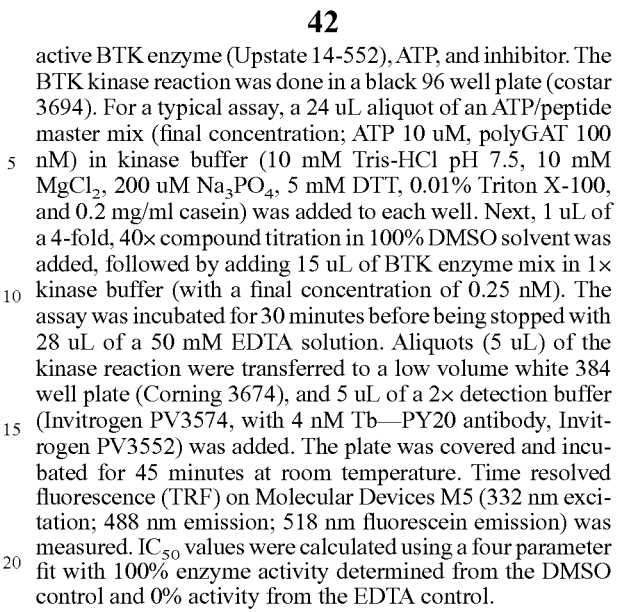

Example 9

Study Protocol to Determine Activation of the PXR Nuclear Receptor in Human DPX2 Cells A) Protocol Summary:

PXR has been shown to be a primary nuclear receptor that mediates drug-induced expression of CYP3A4 (Bertilsson G, et al.; Proc Natl Acad Sci USA. 1998 Oct. 13; 95(21):12208-13). Based on this pathway of CYP3A4 induction, cell-based PXR reporter gene assay is commonly used to screen new molecular entities (NMEs) in early drug discovery stage, for their potential to induce CYP3A4 (Luo G, et al.; Drug Metab Dispos. 2002 July; 30(7):795-804.) Studies were designed to evaluate the effect of NMEs on the activation of human PXR in DPX2 cells. Cell lines stably transfected with the PXR nuclear receptor and corresponding response elements were seeded into 96-well plates. Twenty-four hr after seeding, cells were treated with 6 distinct concentrations of NMEs in triplicate wells (see below), and cells then returned to the incubator for an additional 24 hr. At the end of this incubation period, the number of viable cells/well were determined using Promega's Cell Titer Fluor cytotoxicity assay. Following this assay, Promega's ONE-Glo was added to the same wells and reporter gene activity assessed.

b) Test System:

The test system consisted of the stably transformed DPX2 tumor cell line plated on 96-well microtiter plates. An expression vector harboring the PXR nuclear receptor plus the appropriate enhancers and promoters linked to the luciferase reporter gene have been stably integrated into these tumor cell lines. Receptor activation was assessed by monitoring reporter gene activity, and by comparing the results to vehicle-treated cells. Positive controls consist of cells treated with 6 different concentrations (0.1, 0.5, 1, 5, 10, and 20 µM) of rifampicin. In this manner, compounds activating PXR can be easily and rapidly identified. Since stably-integrated cell lines were used, it is possible to observe from 3- to 70-fold receptor activation.

c) Data Processing and Receptor Activation Kinetics:

Data processed using MS-Excel was calculated as the mean (n=3) and % CV of the fold PXR activation relative to vehicle-treated cells at each of the 6 different doses. All activation data was normalized to the number of viable cells/well. Results were also expressed as a percentage of the response given by the appropriate positive control at a 10 µM dose. $EC_{50}$ and $E_{max}$ values were derived for test compounds that give receptor activation using nonlinear regression of typical log dose-response curves (Prism V5.0c, GraphPad Software, San Diego, Calif.). Agents exhibiting atypical dose-response curves were not analyzed in this fashion.

d) New Molecular Entities (NMEs):

Test compounds were tested at 0.05, 0.1, 0.5, 1, 2.5, and 10 µM

Compound I was tested in the PXR assay and gave PXR % induction (relative to 10 uM rifampin) of less than 30%. Comparator compounds $I^{C1}$ and $I^{C2}$, shown above, produced a PXR % induction of 95% and 88%, respectively.

Example 10

GSH Trapping in Human Liver Microsome: Protocol

Test compound (final concentration 10 uM) was incubated with either human or rat liver microsomes (final concentration 1 mg/mL), along with activating cofactors NADPH (final concentration 1 mM), potassium phosphate (final concentration 100 mM pH 7.4), magnesium chloride (final concentration 3.3 mM) and the trapping agent GSH (final concentration 5 mM). The incubation mixture was incubated for 60 mins at 37° C. and terminated with ice cold acetonitrile (equal volume as incubation mixture) and the supernatents isolated. The supernatants were either injected directly for LC/MS/MS analysis or dried under $N_2$ and reconstituted in water:acetonitrile (80:20) mixture before LC/MS/MS analysis analysis. The corresponding GSH conjugate was evaluated via LC/MS/MS, using a Triple TOF5600/Xevo Qtof MSe.

GSH conjugates for Compound I was detected at comparable levels to $I^{C1}$ and was demonstrated to form 10 times less GSH conjugate compared compound $I^{C2}$.

Example 11

Protocol for FastPatch hERG Inhibition Assay

The cardiac potassium channel, hERG, is responsible for a rapid delayed rectifier current ($I_{Kr}$) in human ventricle and inhibition of $I_{Kr}$ is the most common cause of cardiac action potential prolongation by non-cardiac drugs (see, e.g., Weirich and Antoni, Basic Res. Cardiol., 93, Suppl. 1, 125-32, 1998; Yap and Camm, Clin. Exp. Allergy, 29, Suppl. 3, 174-81, 1999). Increased action potential duration has been cited as a factor in causing prolongation of the QT interval that has been associated with a dangerous ventricular arrhythmia, torsade de pointes (Brown and Rampe, Pharmaceutical News, 7, 15-20, 2000).

The in vitro effects of provided compounds was investigated on the hERG (human ether-à-go-go-related gene) potassium channel current (a surrogate for $I_{Kr}$, the rapidly activating, delayed rectifier cardiac potassium current) expressed in human embryonic kidney (HEK293) cells stably transfected with hERG cDNA. Cells were placed in HEPES-buffered physiological saline solution in a glass-lined 96-well plate and loaded with appropriate amounts of test and control solutions for a duration of a 3-minute exposure at each concentration. Test compound was diluted in 0.3% DMSO. An automated parallel patch clamp system, QPatch HT (Sophion Bioscience A/S, Denmark), was used to evaluate at various concentrations (e.g., 10 µM). The $IC_{50}$ values were estimated based on the hERG inhibition data. The study was performed at ChanTest (14656 Neo Parkway, Cleveland, Ohio). The QPatch screen is further described by Janzen and Bernasconi (eds.), High Throughput Screening, Methods and Protocols, Second Edition, vol. 565, chapter 10, pg. 209-223, 2009.

Compound I gave a hERG $IC_{50}$ of 9.4 uM. Comparator compounds $I^{C1}$ and $I^{C2}$, shown above, produced hERG $IC_{50}$ values of 1.18 uM and 15.18 uM.

Example 12

Rat Collagen-Induced Arthritis Model

The collagen induced arthritis (CIA) model in female Lewis rats requires primary T and B cell immune responses to type II collagen (CII) immunization for the development of a severe inflammatory disease (see Goldschmidt T J, Holmdahl R. Cell Immunol. 154(1):240-8, 1994; Helfgott, S. M., et al; Clin. Immunol. Immunopathol. 31:403, 1984; Holmdahl R. et al., J Autoimmun. 7(6):739-52, 1994; and Stuart, J. M., et al., J. Exp. Med. 155:1, 1982). Clinical disease onsets after a secondary CII challenge and the disease progresses over the following eight days.

Generally, female Lewis rats were immunized with bovine collagen type II in incomplete Freund's adjuvant. Rats (N=10/group) received daily oral administration of Compound I or vehicle BID by oral gavage beginning on day 1 (therapeutic). Clinical severity of arthritis was assessed by caliper measurements of ankles taken every day beginning on Day 0. FIGS. 4A and 4B depict the results of the study, which show that compound I reduced ankle diameter in a dose-dependent manner: therapeutic administration of Compound I ameliorates established disease in rat collagen-induced arthritis (A). Ankle histiopathology $ED_{50}$=4.08 mg/kg; * indicates p<0.05 ANOVA to vehicle control (B).

Detailed protocol: Female Lewis rats were immunized subcutaneously with bovine collagen type II (1:1 emulsion of 2 mg/ml bovine CII in 0.01 N acetic acid: Incomplete Freund's Adjuvant) at three sites of back skin. Six days post immunization rats received a second subcutaneous injection of bovine CII. Compound I suspension or vehicle (0.5% CMC, 0.1% Tween 80) was administered by oral gavage BID beginning on day 0 (prophylactic) (n=10 animals/group).

Clinical severity of CIA was assessed by caliper measurements of ankles taken every day beginning on Day 9. Baseline ankle caliper measurements were taken and confirmed as clinically normal (0.260-0.264 in) for prophylactic treatment. Baseline ankle caliper measurements for established disease animals was assessed on day 1 of therapeutic dosing and animals were randomly assigned to treatment groups after confirmation of clinically disease onset (0.2751-0.2755 in). Data was analyzed across all groups using a one-way analysis of variance (1-way ANOVA), along with an appropriate multiple comparison post-test. Significance for all tests is set at $p \leq 0.05$.

Example 13

Analysis of BCR Pathway Activation Via Inhibition of Phosphorylation of PLCγ2

Protocol: One day before treatment, Ramos cells were plated at a density of $3 \times 10^5$ cells per well in 200 µl, of complete medium in a 96-well tissue culture filter plates (Millipore, Billerica, Mass.). On the day of treatment, used medium was removed by filtration and the cells re-suspended in 200 µL serum free medium containing serial compound dilutions and DMSO to 0.1%, then incubated for 2 hours at 37° C. Cells were stimulated for 5 minutes with 10 µg/mL goat anti-human IgM at 37° C. All medium was removed by filtration and the cells were rinsed with ice cold PBS then lysed on ice for 1 hour with lysis buffer containing; 20 mM Tris (pH 7.5), 150 mM NaCl, 1 mM EDTA, 1 mM EGTA, 2 mM $Na_3VO_4$, 1% Triton X-100, 0.1% SDS, protease inhibitor cocktail, 1 mM phenylmethylsulfonyl fluoride, (PMSF), Phosphatase inhibitor mix 2 (Sigma cat # P5726 from Sigma, St. Louis, Mo.), and Phosphatase inhibitor mix 3 (Sigma cat # P0044 from Sigma, St. Louis, Mo.). Lysates were subsequently transferred to standard MSD plates (Meso Scale Discovery, (MSD), (Gaithersburg, Md.)), pretreated with capture antibody (anti-total PLCγ2 antibody B10, (SantaCruz Biotechnologies (Santa Cruz, Calif.)) and blocked with BSA according to the manufacturer's directions. Lysates were incubated in the prepared MSD plates overnight at 4° C. with gentle agitation. Wells were washed three times with TBST and treated with anti pPLCγ2 (SantaCruz) in 1% BSA in PBS for 1 hour at room temperature. Wells were again washed three times with TBST and treated with anti-rabbit sulfo-tag antibody (MSD), for 1 hour at room temperature. After washing with TBST, MSD read buffer was added and the luminescence was measured in an MSD SECTOR Imager 6000. Maximum response was determined as the average luminescence in wells containing stimulated cells treated with anti-IgM and DMSO. Minimal response was determined as the average luminescence in wells containing unstimulated cells treated with DMSO alone. The maximal and minimal values were used to normalize luminescence in compound treatment wells. The normalized values were plotted against compound concentration on a log scale then analyzed using Prizm software (GraphPad Software, Inc.). A sigmoidal dose-response equation with variable slope was used to fit the data and generate 50% inhibition concentration ($IC_{50}$). The results are depicted in FIG. 5.

Compound I exhibits a calculated $EC_{50}$ of 150 nM using an electrochemical luminescent immunoassay. Ramos cells were incubated in 96 well plates with a range of concentrations of Compound I for 2 hours, stimulated with 10 µg/mL anti-IgM for 5 minutes, and PLCγ2 phosphorylation measured using an electrochemical-luminescent immunoassay. The $EC_{50}$ was calculated using GraphPad Prism software and determined to be 150 nM. ($R^2=0.90$).

Example 14

Inhibition BCR-Induced Human B Cell Proliferation

Human CD19+ B cells were stimulated with an anti-IgM antibody and the activity of Compound I was evaluated in terms of altering cellular metabolism after 72 hours. In this context, cellular metabolism directly correlates with cellular activation and proliferation, and can also reflect relative cell survival during proliferation. Anti-IgM antibody was evaluated for effects on B cell proliferation and determined to exhibit a half-maximal concentration for activation of 10 µg/ml. Using these activation conditions, varying concentrations of Compound I were assayed, in triplicate in 0.1% DMSO, for impact on cellular metabolism of CD19+ B cells isolated from different donors. Compound I exhibited dose-dependent inhibition of anti-IgM-induced B cell cellular metabolism, with an $IC_{50}$ of 260+/−76 nM. The results are shown graphically in FIG. 6.

Protocol: Human B cells were isolated from peripheral blood mononuclear cells or unpurified buffy coats using Ficoll-Hypaque gradients (Amersham) and negatively selected by magnetic cell sorting (Human B Cell Isolation Kit II, Miltenyi Biotec). Target cell purity was determined by flow cytometry by staining for markers of B cells, T cells and monocytes (CD19, CD3, CD14, respectively; BD Biosciences). Data was collected on a FACsCaliber flow cytometer and analyzed using FloJo software (BD Biosciences). Purity of human B cell preparations was routinely greater than 95%. Negatively selected human B cells were stimulated with 10 µg/mL anti-IgM F(ab')$_2$ (Jackson ImmunoResearch) in 96 well plates. 100,000 B cells in 0.2 mL RPMI+10% FBS were treated with varying concentrations (titrated from 5000 nM to 0 nM in 0.5% DMSO) of Compound I in triplicate wells or vehicle control in 0.5% DMSO final concentration for 30 minutes at 37° C., 5% CO2, then cells were stimulated with 10 µg/mL anti-IgM F(ab')2. B cells were stimulated for 72 hr at 37° C., 5% CO2. Proliferation was measured using the CellTiter-Glo reagent (Promega), as measured on a luminometer. Mean values were plotted against maximum proliferation and $IC_{50}$ values were determine using GraphPad Prism v5 software.

Example 15

Evaluation of the Effect of Compound I on Myeloid Cell Activation In Vitro

FcγR activation of primary human macrophages. Autoantibody and immune-complex mediated activation through FcγR can be modeled by activation of macrophages with immobilized IgG. Primary human macrophages derived from GM-CSF treated monocytes up-regulate activation markers such as CD80, CD86, MHC antigens and the FcγRIII receptor. Human monocyte derived macrophages can be activated by plate-bound purified human IgG. This stimulation crosslinks the FcγRIII receptor and induces the secretion of pro-inflammatory cytokines such as TNFα, IL-6, IL 1β and MCP-1. Compound I was evaluated for inhibition of cytokine expression following FcR activation of human macrophages. Compound I inhibited TNFα and IL-6 expression with an $IC_{50}=1.1$ µM and 0.35 µM, respectively).

Generally, macrophages were cultured in plates previously incubated with purified IgG then washed. Titrations of compound I (10,000 nM to 0 nM) were added to these cultures. Cell culture supernatants were analyzed by ELISA for the expression of TNFα and IL-6. Compound I inhibited the secretion of these cytokines in a dose dependent manner, producing an $IC_{50}$ for inhibition of TNFα of 1077 nM (FIG. 7A), and for inhibition of IL-6 of 350 nM (FIG. 7B).

Protocol: Human monocytes were isolated from buffy coats of healthy donors and negatively selected by magnetic cell sorting (Monocyte Isolation Kit II, Miltenyi Biotec). Purified monocytes were cultured in standard media supplemented with low-IgG FBS and 100 ng/mL GM-CSF for 5-7 days to induce macrophage differentiation. Cultured macrophages were stimulated with 100 µg/mL plate-bound purified IgG±a titration of compound I (10 µM to 0 nM). Supernatants were collected after 4 hrs and 18 hrs and analyzed for TNFα and IL-6, respectively.

Example 16

Compound I Exhibits Dose Dependent Efficacy in Mouse Collagen Antibody-Induced Arthritis This Example relates not only to arthritis, but also evaluates the activity of autoantibodies and immune complexes in vivo and therefore is relevant to other inflammatory disorders such as SLE. In this experiment, the activity of autoantibodies and immune complexes produce a pathological endpoint that is dependent on FcR signalling, and the Fc portion of such antibodies is inhibited by administration of compound I.

The collagen antibody-induced arthritis (CAIA) model in female DBA/1 mice does not require cognate T and B cell responses for the induction of inflammation but rather relies on immune effector mechanisms for the development of clinical disease. A cocktail of four anti-collagen II (CII) specific monoclonal antibodies and immune stimulatory lipopolysaccharide (LPS) administered 3 days after CII specific antibody transfer promote antibody-Fc-Receptor engagement (Kagari T. et al.; *J Immunol.* 170:4318-24 (2003)), immune complex formation, complement activation (Banda N K, et al.; *Clin Exp Immunol.* 159:100-8 (2010)) and pro-inflammatory cytokine production to induce a severe inflammatory disease over a 10 day period.

Generally, arthritis was induced by injection of a cocktail of monoclonal anti-collagen antibodies into DBA/1 mice on day 0. Mice (N=10/group) received daily oral administration of compound I either QD or BID as indicated beginning on day 0. Paw inflammation was evaluated daily. Each point represents the mean arthritis index±SEM for animals in a group. See FIG. 8.

Protocol: Female DBA/1 mice 6-8 weeks of age received 2 mg of an arthitogenic four clone monoclonal antibody cocktail (Chondrex#10100) i.v. on day 0 followed by a 50 ug dose of LPS on 3 days later. Compound I suspension or vehicle (0.5% CMC, 0.1% Tween 80) was administered BID by oral gavage beginning on day 0 (10 animals/group) just prior to i.v. transfer of antibody cocktail. Clinical severity of CIA was assessed by monitoring inflammation on all four paws, applying a scale ranging from 0 to 4. Each paw was graded as follows: 0, normal; 1, mild but definite redness and swelling of the ankle or wrist, or redness and swelling of any severity for 1 or 2 digits; 2, moderate to severe redness and swelling of the ankle or wrist, or more than two digits; 3, redness and swelling (pronounced edema) of the entire paw; and 4, maximally inflamed limb with involvement of multiple joints. The sum of the four individual scores was the arthritis index, with a maximal possible score of 16 for each animal.

What is claimed is:

1. A compound:

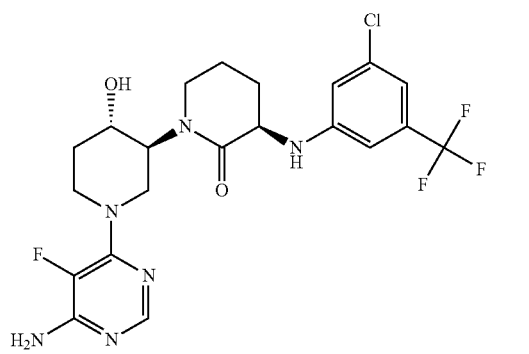

Compound I or a pharmaceutically acceptable salt thereof.

2. A solid form of Compound I:

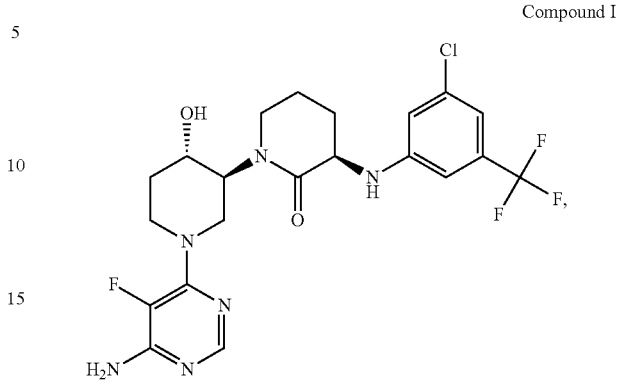

Compound I wherein Compound I is a free base.

3. The solid form of claim 2, wherein the solid form is Form 1.

4. The solid form of claim 3, having one or more peaks in its X-ray powder diffraction pattern selected from those at 9.708, about 11.174, about 12.485, about 15.558, about 16.293, about 16.790, about 17.470, about 18.550, about 18.966, about 20.776, about 22.439, about 23.347, about 24.551, about 25.028, about 26.167, about 28.152, about 29.739, and about 33.922 degrees 2-theta.

5. The solid form of claim 4, having substantially all of the peaks in its X-ray powder diffraction pattern selected from those at about:

| Angle 2-Theta ° | Angle 2-Theta ° |
| --- | --- |
| 9.708 | 20.776 |
| 11.174 | 22.439 |
| 12.485 | 23.347 |
| 15.558 | 24.551 |
| 16.293 | 25.028 |
| 16.790 | 26.167 |
| 17.470 | 28.152 |
| 18.550 | 29.739 |
| 18.966 | 33.922. |

6. The solid form of claim 2, wherein the solid form is Form 2.

7. The solid form of claim 6, having one or more peaks in its X-ray powder diffraction pattern selected from those at about 7.834, about 8.826, about 9.886, about 13.030, about 14.429, about 16.779, about 18.108, about 19.835, about 20.561, about 22.426, and about 24.089 degrees 2-theta.

8. The solid form of claim 7, having substantially all of the peaks in its X-ray powder diffraction pattern selected from those at about:

| Angle 2-Theta ° | Angle 2-Theta ° |
| --- | --- |
| 7.834 | 18.108 |
| 8.826 | 19.835 |

| Angle 2-Theta ° | Angle 2-Theta ° |
|---|---|
| 9.886 | 20.561 |
| 13.030 | 22.426 |
| 14.429 | 24.089. |
| 16.779 | |

9. A composition comprising the compound of claim 1 and a pharmaceutically acceptable carrier or excipient.

10. A composition comprising the solid form of claim 2 and a pharmaceutically acceptable carrier or excipient.

11. A method of decreasing the enzymatic activity of Bruton's tyrosine kinase comprising contacting Bruton's tyrosine kinase with an effective amount of a compound of claim 1 or a composition thereof.

12. A method of treating a disorder selected from the group consisting of rheumatoid arthritis, systemic lupus erythematosus, leukemia, or lymphoma comprising administering to a human subject an effective amount of a compound of claim 1 or a composition thereof.

13. A method comprising the steps of:
a) providing a pyrrolidinone of formula A:

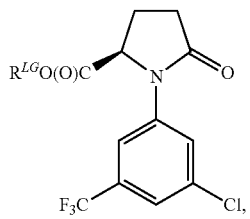

A wherein —OR$^{LG}$ is a suitable leaving group; and
b) contacting the pyrrolidinone of formula A with a suitable reducing agent to provide a hemiaminal of formula B:

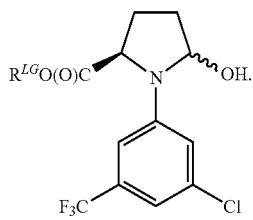

B

14. The method of claim 13, further comprising the steps of:
a) providing an amino alcohol of formula C:

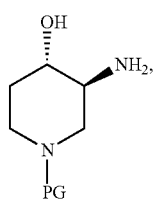

C wherein PG is a suitable protecting group; and
b) reacting the amino alcohol of formula C with the hemiaminal of formula B under suitable conditions to provide an ester of formula D:

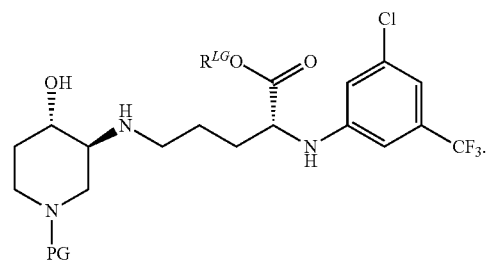

D

15. The method of claim 14, further comprising the step of reacting the ester of formula D under suitable conditions to provide a lactam of formula E:

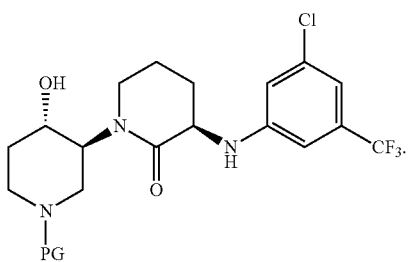

E

16. The method of claim 15, further comprising the step of deprotecting the lactam of formula E to provide a compound of formula F:

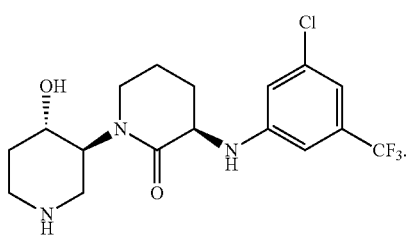

F

17. The method of claim 16, further comprising the steps of:
a) providing pyrimidine G:

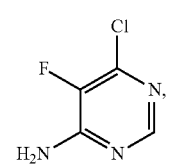

G and b) contacting the pyrimidine G with the compound of formula F under suitable conditions to provide compound I:

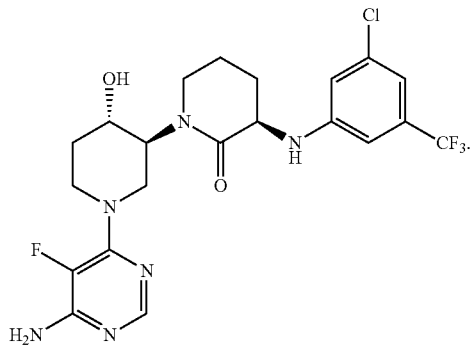

18. The method of claim 13, further comprising the steps of:

a) providing amino alcohol J:

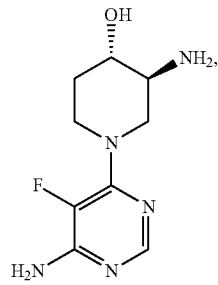

and b) reacting amino alcohol J with the hemiaminal of formula B under suitable conditions to provide an ester of formula K:

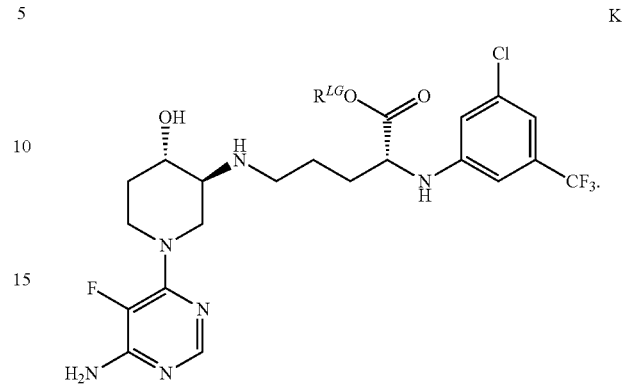

19. The method of claim 18, further comprising the step of reacting the ester of formula K with a suitable base to provide compound I:

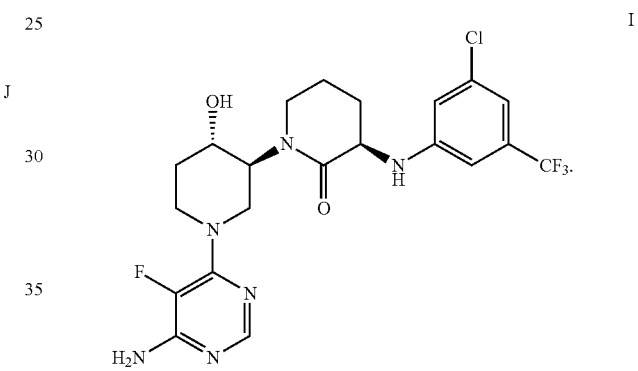

* * * * *